United States Patent [19]
Shirakawa et al.

[11] Patent Number: 6,114,507
[45] Date of Patent: Sep. 5, 2000

[54] ANTI-FAS LIGAND ANTIBODY AND ASSAY METHOD USING THE ANTI-FAS LIGAND ANTIBODY

[75] Inventors: Kamon Shirakawa; Tomokazu Matsusue, both of Tokyo; Shigekazu Nagata, Osaka-fu, all of Japan; Man Sung Co, Cupertino; Maximiliano Vasquez, Palo Alto, both of Calif.

[73] Assignees: Mochida Pharmaceutical Co., Ltd., Tokyo; Osaka Bioscience Institute, Osaka-fu, both of Japan

[21] Appl. No.: 08/649,100

[22] Filed: May 17, 1996

[30] Foreign Application Priority Data

Jun. 30, 1995 [JP] Japan ................................. 7-188480

[51] Int. Cl.[7] .............................. C07K 16/00; C12N 5/00; A61K 39/395; A61K 39/00
[52] U.S. Cl. ................... 530/389.2; 435/326; 424/145.1; 424/185.1
[58] Field of Search ......................... 530/389.2; 435/326; 424/145.1, 185.1

[56] References Cited

FOREIGN PATENT DOCUMENTS

| WO9513293 | 5/1995 | WIPO . |
| WO9518819 | 7/1995 | WIPO . |
| WO96/29350 | 9/1996 | WIPO . |

OTHER PUBLICATIONS

Tanaka et al. (1995) The EMBO Journal vol. 14, No. 6, pp. 1129–1135.
Man Sung Co. et al. (1991) Proc. Natl. Acad. Aci, USA, vol. 88, pp. 2869–2873.
Riechmann et al. (1988) Nature, vol. 332, pp.323–327.
Man Sung Co. et al. (1992) The Journal of Immunology, vol.148, 1149–1154, No. 4.
Tanaka et al. (1996) Nature Medicine, vol. 2, No. 3, pp.317–322.
Queen et al. (1989) Proc. Natl. Acad. Sci, USA, vol. 86, pp. 10029–10033.
Man Sung Co., et al. (1994) The American Assoc. of Immunologiest, pp. 2968–2976.
Kayagaki et al, J. Exp. Med., vol. 182, No. 6, pp. 1777–1783 (Dec. 1995).
Yonehara et al., A cell–killing monoclonal antibody (Anti–Fas) to a cell surface antigen co–downregulated with the receptor of tumor necrosis factor, J. Exp. Med., 169, 1747–1756, May 1989.
Takahashi et al., Human Fas ligand: gene structure, chromosomal location and species specificity, Int. Immunol., 6(10), 1567–1574, Jun. 1994.
Mariani et al., Eur. J. Immunol. 25:2303–2307 (1995).

*Primary Examiner*—Jeffrey Stucker
*Assistant Examiner*—Hankyel T. Park
*Attorney, Agent, or Firm*—Birch, Stewart, Kolasch & Birch, LLP

[57] ABSTRACT

An anti-Fas ligand antibody capable of suppressing Fas ligand-induced apoptosis to a high degree, especially humanized antibodies having less antigenecity to human, and a method for assaying the Fas ligand in human body fluid utilizing such an antibody.

Measurement of the Fas ligand in human body fluid would be useful for elucidation of hepatitis B, hepatitis C, HIV infections and the like, and for prediction and diagnosis of pathological conditions associated with such diseases.

23 Claims, 17 Drawing Sheets

| Peptide No. | Amino acid sequence |
|---|---|
| M52 | SLEKQIGHPSPPPEKKELRK |
| M53 | LTGKSNSRSMPLEW |
| M54 | WEDTYGIVLLSGV |
| M55 | LVINETGLYFV |
| M56 | VYSKVYFRGQSCNNLPLSH |
| M57 | KVYMRNSKYPQDLVMMEG |
| M58 | KMMSYCTTGQMWARSS |
| M59 | LVNFEESQTFF |

FIG.1

```
         10         20         30         40         50         60         70
QLFHLQKELAELRESTSQMHTASSLEKQIGHPSPPPEKKELRKVAHLTGKSNSRSMPLEWEDTYGIVLLSGVKYK
                        |_____|  |_____|  |_____|
         80         90        100        110        120        130        140
KGGLVINETGLYFVYSKVYFRGQSCNNLPLSHKVYMRNSKYPQDLVMMEGKMMSYCTTGQMWARSSYLGAV
   |_____|  |_____|  |_____|  |_____|
        150        160        170    179
FNLTSADHLYVNVSELSLVNFEESQTFFGLYKL
                 |_____|
```

| Peptide No. | Amino acid sequence |
|---|---|
| M52 | SLEKQIGHPSPPPEKKELRK |
| M53 | LTGKSNSRSMPLEW |
| M54 | WEDTYGIVLLSGV |
| M55 | LVINETGLYFV |
| M56 | VYSKVYFRGQSCNNLPLSH |
| M57 | KVYMRNSKYPQDLVMMEG |
| M58 | KMMSYCTTGQMWARSS |
| M59 | LVNFEESQTFF |

FIG. 10

```
                                    30                                              60
ATG ATG TCC TCT GCT CAG TTC CTT GGT CTC CTG TTG CTC TGT TTT CAA GGT ACC AGA TGT
 M   M   S   S   A   Q   F   L   G   L   L   L   L   C   F   Q   G   T   R   C 90                                             120
GAT ATC CAG ATG ACA CAG ACT ACA TCC TCC CTG TCT GCC TCT CTG GGA GAC AGA GTC ACC
 D   I   Q   M   T   Q   T   T   S   S   L   S   A   S   L   G   D   R   V   T
 =

150                                             180
ATC AGT TGC AGG GCC AGT CAG GAC ATT AGC AAT TAT TTA AAC TGG TAT CAG CAG AAA CCA
 I   S   C   R   A   S   Q   D   I   S   N   Y   L   N   W   Y   Q   Q   K   P 210                                             240
GAT GGA ACT GTT AAA CTC CTG ATC TAC TAC ACA TCA AGA TTA CAC TCA GGA GTC CCA TCA
 D   G   T   V   K   L   L   I   Y   Y   T   S   R   L   H   S   G   V   P   S 270                                             300
AGG TTC AGT GGC AGT GGG TCT GGG ACA AAT TAT TCT CTC ACC ATT AGC AAC CTG GAA CAA
 R   F   S   G   S   G   S   G   T   N   Y   S   L   T   I   S   N   L   E   Q 330                                             360
GGA GAT ATT GCC ACT TAC TTT TGC CAA CAG GGT AGT ACG CTT CCG TGG ACG TTC GGT GGA
 G   D   I   A   T   Y   F   C   Q   Q   G   S   T   L   P   W   T   F   G   G

GGC ACC AAG CTG GAA ATC AAA
 G   T   K   L   E   I   K
```

FIG. 11

```
                            30                                              60
ATG GAT TGG GTG TGG ACC TTG CTA TTC CTG ATA GCA GCT GCC CAA AGT GCC CAA GCA CAG
 M   D   W   V   W   T   L   L   F   L   I   A   A   A   Q   S   A   Q   A   Q 90                                             120
ATC CAG TTG GTG CAG TCT GGA CCT GAG CTG AAG AAG CCT GGA GAG ACA GTC AAG ATC TCC
 I   Q   L   V   Q   S   G   P   E   L   K   K   P   G   E   T   V   K   I   S 150                                             180
TGC AAG GCT TCT GGG TAT ACC TTC ACA GAA TAT CCA ATG CAC TGG GTG AAG CAG GCT CCA
 C   K   A   S   G   Y   T   F   T   E   Y   P   M   H   W   V   K   Q   A   P 210                                             240
GGA AAG GGT TTC AAG TGG ATG GGC ATG ATA TAC ACC GAC ACT GGA GAG CCA TCA TAT GCT
 G   K   G   F   K   W   M   G   M   I   Y   T   D   T   G   E   P   S   Y   A 270                                             300
GAA GAG TTC AAG GGG CGG TTT GCC TTC TCT TTG GAG ACC TCT GCC AGC ACT GCC TAT TTG
 E   E   F   K   G   R   F   A   F   S   L   E   T   S   A   S   T   A   Y   L 330                                             360
CAG ATC AAC TTC CTC AAA AAT GAG GAC ACG GCT ACA TAT TTC TGT GTA AGA TTT TAC TGG
 Q   I   N   F   L   K   N   E   D   T   A   T   Y   F   C   V   R   F   Y   W

390
GAT TAC TTT GAC TAC TGG GGC CAA GGC ACC ACT CTC ACA GTC TCC TCA
 D   Y   F   D   Y   W   G   Q   G   T   T   L   T   V   S   S
```

FIG. 12

```
                              30                                          60
ATG GAG ACC GAT ACC CTC CTG CTA TGG GTC CTC CTG CTA TGG GTC CCA GGA TCA ACC GGA
 M   E   T   D   T   L   L   L   W   V   L   L   L   W   V   P   G   S   T   G 90                                         120
GAT ATT CAG ATG ACC CAG AGT CCG TCG ACC CTC TCT GCT AGC GTC GGG GAT AGG GTC ACC
 D   I   Q   M   T   Q   S   P   S   T   L   S   A   S   V   G   D   R   V   T
 =

150                                         180
ATA ACT TGC AGG GCA AGT CAG GAC ATT TCG AAT TAT TTA AAC TGG TAT CAG CAG AAG CCA
 I   T   C   R   A   S   Q   D   I   S   N   Y   L   N   W   Y   Q   Q   K   P 210                                         240
GGC AAA GCT CCC AAG CTT CTA ATT TAT TAC ACA TCA AGA TTA CAC TCA GGG GTA CCT TCA
 G   K   A   P   K   L   L   I   Y   Y   T   S   R   L   H   S   G   V   P   S 240                                         270
CGC TTC AGT GGC AGT GGA TCT GGG ACC AAT TAT ACC CTC ACA ATC TCG AGT CTG CAG CCA
 R   F   S   G   S   G   S   G   T   N   Y   T   L   T   I   S   S   L   Q   P 330                                         360
GAT GAT TTC GCC ACT TAT TTT TGC CAA CAG GGT AGT ACG CTT CCG TGG ACG TTC GGT CAG
 D   D   F   A   T   Y   F   C   Q   Q   G   S   T   L   P   W   T   F   G   Q

GGG ACC AAG GTG GAG GTC AAA
 G   T   K   V   E   V   K
```

FIG. 13

```
                        30                                              60
ATG GAT TGG GTG TGG ACC TTG CTA TTC CTG ATA GCT GCA GCC CAA AGT GCC CAA GCA CAG
 M   D   W   V   W   T   L   L   F   L   I   A   A   A   Q   S   A   Q   A   Q 90                                             120
GTC CAG TTG GTG CAG TCT GGA GCT GAG GTG AAG AAG CCT GGA AGC TCA GTC AAG GTG TCC
 V   Q   L   V   Q   S   G   A   E   V   K   K   P   G   S   S   V   K   V   S 150                                             180
TGC AAA GCT TCT GGG TAT ACC TTC ACA GAA TAT CCA ATG CAC TGG GTG AGA CAG GCT CCA
 C   K   A   S   G   Y   T   F   T   E   Y   P   M   H   W   V   R   Q   A   P 210                                             240
GGA CAG GGT TTC AAG TGG ATG GGC ATG ATA TAC ACC GAC ACT GGA GAG CCA TCA TAT GCT
 G   Q   G   F   K   W   M   G   M   I   Y   T   D   T   G   E   P   S   Y   A 270                                             300
GAA GAG TTC AAG GGA CGG TTT ACA TTC ACT TTG GAC ACC TCT ACC AAC ACT GCC TAT ATG
 E   E   F   K   G   R   F   T   F   T   L   D   T   S   T   N   T   A   Y   M 330                                             360
GAG CTC AGC TCT CTC AGG TCT GAG GAC ACG GCT GTC TAT TAC TGT GTA AGA TTT TAC TGG
 E   L   S   S   L   R   S   E   D   T   A   V   Y   Y   C   V   R   F   Y   W

390
GAT TAC TTT GAC TAC TGG GGT CAA GGT ACC CTG GTC ACA GTC TCC TCA
 D   Y   F   D   Y   W   G   Q   G   T   L   V   T   V   S   S
```

ANTI-FAS LIGAND ANTIBODY AND ASSAY METHOD USING THE ANTI-FAS LIGAND ANTIBODY

BACKGROUND OF THE INVENTION

This invention relates to an anti-Fas ligand antibody and an assay method utilizing the anti-Fas ligand antibody. More specifically, this invention relates to a method for assaying a Fas ligand in human body fluid utilizing an anti-Fas ligand antibody, and the antibody adapted for use in such an assay. This invention also relates to an anti-Fas ligand antibody that exhibits high suppression of the Fas ligand-induced apoptosis. This invention also relates to a hybridoma or a cell line that produces such an antibody.

Human Fas ligand is a polypeptide that has been reported by Nagata et al. to be a biological molecule that induces apoptosis of Fas antigen-expressing cells (Takahashi, T. et al., International Immunology, vol. 6, 1567–1574, 1994). Human Fas ligand is a Type II membrane protein of TNF family with a molecular weight of about 50 kD. As in the case of TNF, human Fas ligand in the human body is estimated to be in the form of a trimer (Tanaka, M. et al., EMBO Journal, vol. 14, 1129–1135, 1995). The extracellular domain of the human Fas ligand is highly homologous with the extracellular domain of rat Fas ligand (Suda, T. et al., Cell, vol. 75, 1169–1178, 1993) and mouse Fas ligand (Takahashi, T. et al., Cell, vol. 76, 969–976, 1994). The human Fas ligand recognizes not only human Fas antigen but also mouse Fas antigen, and the apoptosis is induced after such recognition of the Fas antigen. At the same time, the rat Fas ligand and the mouse Fas ligand recognize the human Fas antigen to induce the apoptosis.

Apoptosis has called attention for its deep involvement in homeostasis of an organism. The homology of the Fas ligands among different species as mentioned above suggests the important role of the apoptosis mediated by the Fas ligand and the Fas antigen in the homeostasis of organism.

Recently, an interesting relation of abnormality of Fas ligand and Fas antigen with an autoimmune disease has been reported. In this report, there is suggested that MRL-lpr/lpr (a strain of model mouse for an autoimmune disease) has mutation in its Fas antigen gene, and apoptosis is not induced in the cells expressing such mutant Fas antigen gene (Watanabe-Fukunaga, R. et al, Nature, vol. 356, 314–317, 1993; Adachi, M. et al., Proc. Natl. Acad. Sci. USA, vol. 90, 1993). In the meanwhile, there has also been reported that C3H-gld/gld (another strain of model mouse for an autoimmune disease) has mutation in its Fas ligand gene, and that the Fas ligand of the gld mouse has no apoptosis-inducing activity. The mutation in the Fas ligand gene of the gld mouse is a point mutation, and as a result of such point mutation, 7th amino acid from the C terminal of the extracellular domain of the Fas ligand is replaced with another amid acid (Takahashi, T. et al., Cell, vol. 76, 969–976, 1994). The Fas ligand the gld mouse as described above is incapable of binding with the Fas antigen (Ramsdell, F. et al., Eur. J. Immunol., vol. 24, 928–933, 1994).

The findings as described above resulted in the hypothesis that some autoimmune diseases are induced by the abnormality of the Fas antigen or the Fas ligand, namely, by the autoreactive T cells remaining in the body that should have been removed from the body by undergoing apoptosis if the cells had been normal.

Recently, it is conceived that abnormal propagation of synovial membrane that takes place in rheumatism is also induced by the failure of normal apoptosis of the cell. Kobayashi, N. et al. further estimates that reduction in the number of T cells upon infection by AIDS virus is mediated by the Fas ligand since expression of the Fas antigen on the T cell membrane is induced upon infection by the AIDS virus (Nikkei Science, vol. 6, 34–41, 1993).

As the relation between the apoptosis mediated by the Fas ligand-Fas antigen and the diseases is gradually found out, a growing expectation is present for the use of the Fas ligand or the Fas antigen in the treatment of the diseases associated with abnormality of the apoptosis, such as the above-mentioned autoimmune diseases, rheumatism and AIDS.

Nagata et al. have also reported that they succeeded in obtaining an antibody against the Fas ligand, and that such antibody was capable of suppressing the apoptosis (Tanaka, M. et al., EMBO Journal, vol. 14, 1129–1135, 1995; International Patent Application Laid-Open No. WO95/13293).

Nagata et al. have made further investigation on an N terminal-deleted Fas ligand and succeeded in creating a Fas ligand with higher activity (International Patent Application No. PCT/JP95/00883).

As described above, Nagata et al. have made a series of intensive studies to isolate the Fas ligand, and prepared an antibody against such Fas ligand.

However, there has so far been no report of actual measurement of the Fas ligand in the human body fluid, and presence of a soluble Fas ligand in the human body fluid has remained unconfirmed. It is generally conceived that a physiologically active cytokine such as Fas ligand is topically produced in a minute amount to topically madiate an action. Such cytokine usually has a short half life, and after mediating an action, the cytokine is rapidly discharged from the tissue or blood. Therefore, a cytokine such as Fas ligand is not readily detectable in peripheral blood. Fas ligand was originally reported as a transmembrane (membrane-bound) protein, and release of the Fas ligand from the cell under some special conditions is indicated in an in vitro experiment (Tanaka, M. et al., EMBO Journal, vol. 14, 1129–1135, 1995). Occurrence of such phenomenon under in vivo, physiological conditions has been unknown, and presence of the Fas ligand in human body fluid has also been unknown. Even if the Fas ligand was present in the human body fluid, the concentration of the Fas ligand has been estimated to be very low, and measurement of the Fas ligand at such a low concentration has been regarded quite difficult. In addition, various immunoassay-interfering substances are likely to be present in a body fluid, and therefore, development of a Fas ligand assay system with a high sensitivity and a high specificity and an antibody adapted for such an assay has been required. In view of the relation between the Fas ligand and various diseases indicated, measurement of the Fas ligand concentration in the body fluid is deemed clinically valuable as a means for diagnosing such diseases. However, there has so far been no report directed to the fluctuation of the Fas ligand concentration in the body fluid. In view of the future administration of the Fas ligand or a substance that may affect the activity or expression of the Fas ligand to patients suffering from a disease for which administration of an apoptosis-inducing substance such as Fas ligand might be effective, it is necessary to enable measurement of the Fas ligand concentration in the body fluid to thereby monitor the blood concentration and determine the therapeutic effects. A Fas ligand assay method of high sensitivity and specificity has thus been awaited. With regard to the neutralizing antibody, a neutralizing antibody of a higher neutralizing activity and clarification of the action mechanism has been awaited, and in view of the therapeutic application, an antibody capable of suppressing the apoptosis at a low dosage has been awaited for both effectivity and safety.

Unfortunately, the use of non-human monoclonal antibodies such as mouse monoclonal antibodies have certain drawbacks in human treatment, particularly in repeated therapeutic regimens as explained below. Mouse monoclonal antibodies, for example, have a relatively short circulating half-life, and lack other important immunoglobulin functional characteristics when used in humans.

Perhaps more importantly, non-human monoclonal antibodies contain substantial stretches of amino acid sequences that will be immunogenic when injected into a human patient. Numerous studies have shown that, after injection of a foreign antibody, the immune response elicited by a patient against an antibody can be quite strong, essentially eliminating the antibody's therapeutic utility after an initial treatment. Moreover, as increasing numbers of different mouse or other antigenic (to humans) monoclonal antibodies can be expected to be developed to treat various disease, after one or several treatments with any different non-human antibodies, subsequent treatments even for unrelated therapies can be ineffective or even dangerous in themselves, because of cross-reactivity.

While the production of so-called "chimeric antibodies" (e.g., mouse variable regions joined to human constant regions) has proven somewhat successful, a significant immunogenicity problem remains. In general, the production of human immunoglobulins reactive with Fas ligand, as with many antigens, would be extremely difficult using typical human monoclonal antibody production techniques. Similarly, utilizing recombinant DNA technology to produce so-called "humanized" or "reshaped" antibodies (see, e.g., Riechmann et al., Nature 332, 323 (1988) and EPO Publication No. 0239400, which are incorporated herein by reference), provides uncertain results, in part due to unpredictable binding affinities of the resultant immunoglobulins. In addition, an antibody that reacts with a particular peptide derived from the Fas ligand, namely, an antibody whose binding site within the Fas ligand has been found out, has been awaited for a further investigation of the Fas ligand and analysis of the Fas ligand function.

SUMMARY OF THE INVENTION

An object of the present invention is to provide an anti-Fas ligand antibody and an assay method utilizing such an antibody, and in particular, a method for assaying a Fas ligand in human body fluid using an anti-Fas ligand antibody, and an antibody adapted for use in such assay method. Another object of the present invention is to provide an anti-Fas ligand antibody exhibiting high suppression of the apoptosis induced by the Fas ligand, and said antibody which is a humanized antibody. A further object of the present invention is to provide a hybridoma and cell line producing such an antibody. Furthermore the present invention also provides novel compositions or medicaments containing as an active ingredient at least any one of aforementioned anti-Fas ligand antibodies of the invention, and methods of treating systemic or topical pathological conditions or a disease with, caused by or involving the abnormality of Fas/Fas ligand system or of apoptosis through Fas antigen.

BRIEF DESCRIPTION OF THE DRAWINGS

FIG. 1. A schematic view showing the predicted epitope region in the extracellular domain of the human Fas ligand, and the amino acid sequences or the peptides in the predicted epitope region.

FIG. 10. Sequences of the cDNA and translated amino acid sequences of the light chain variable region of the murine F919 antibody. The complementarity determining regions (CDRs) are underlined and the first amino acid of the mature chain is double underlined.

FIG. 11. Sequences of the cDNA and translated amino acid sequences of the heavy chain variable regions of the murine F919 antibody. The complementarity determining regions (CDRs) are underlined and the first amino acid of the mature chain is double underlined.

FIG. 12. Sequences of the DNA and translated amino acid sequences of the light chain variable regions of the humanized F919 antibody, version 2. The complementarity determining regions (CDRs) are underlined and the first amino acid of the mature chain is double underlined.

FIG. 13. Sequences of the DNA and translated amino acid sequences of the heavy chain variable regions of the humanized F919 antibody, version 2. The complementarity determining regions (CDRs) are underlined and the first amino acid of the mature chain is double underlined.

DETAILED DESCRIPTION OF THE INVENTION

Figure 2:
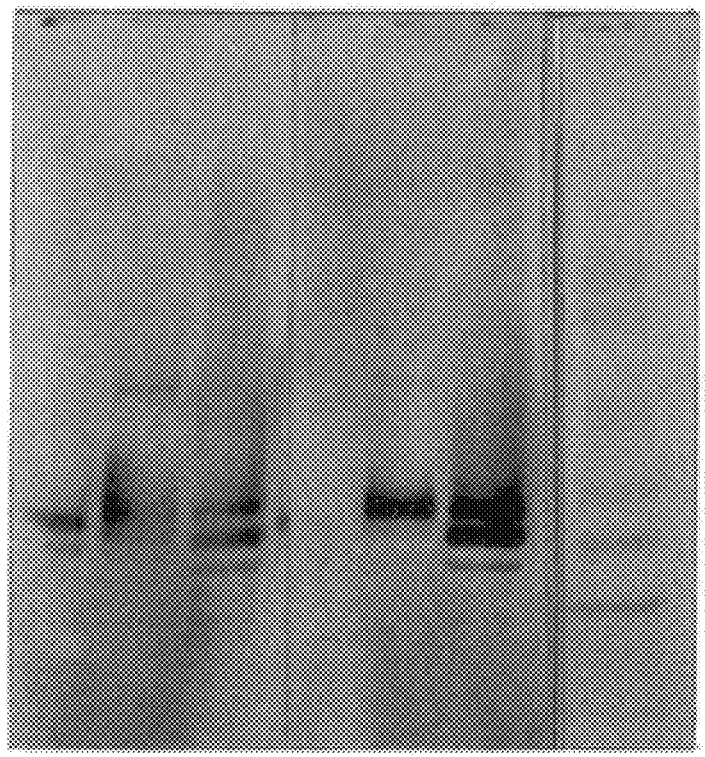
FIG. 2. A photograph for substitution of the drawing showing the results of the western blotting of the Fas ligand using anti-M52 peptide monoclonal antibody.

The present invention is hereinafter described in detail.

The antibodies as described below are provided by the present invention.

[1] An anti-Fas ligand neutralizing antibody (hereinafter sometimes referred to as a neutralizing antibody) which is (1) an anti-Fas ligand antibody with an activity of suppressing Fas ligand-induced apoptosis of Fas antigen-expressing cells at a high degree, exhibiting an apoptosis suppression rate of 50% or higher at 30 μg/ml, preferably 10 μg/ml, and more preferably 3 μg/ml, still more preferably 1 μg/ml, and most preferably 0.3 μg/ml;

(2) an anti-Fas ligand antibody which recognizes at least one of the biologically active Fas ligands;

(3) an anti-Fas ligand antibody which does not recognize at least one of the biologically inactive Fas ligands;

(4) an anti-Fas ligand antibody provided with the characteristics of (2) and (3);

(5) an anti-Fas ligand antibody according to (2) or (4) wherein said biologically active Fas ligand is at least one of the extracellular domain of the Fas ligand; free Fas ligand; polypeptides nd5, nd12, nd20, nd32 and nd42 which are deletion mutants of the extracellular domain of the Fas ligand; and L179F which is a substitution mutant of the extracellular domain of the human Fas ligand, as described in the Examples;

(6) an anti-Fas ligand antibody according to (3), (4) or (5) wherein said biologically inactive Fas ligand is at least one of polypeptide nd49 which is a deletion mutant of the extracellular domain of the Fas ligand; polypeptide cd179 which is a deletion mutant of the extracellular domain of the Fas ligand; and a Fas ligand denatured by aggregation through salting out with ammonium sulfate.

(7) an anti-Fas ligand antibody provided with the characteristics of (1) and (2).

(8) an anti-Fas ligand antibody which binds to human Fas ligand with an affinity constant of at least $10^7 M^{-1}$, preferably $10^8 M^{-1}$, more preferably $10^9 M^{-1}$ and especially $10^{10} M^{-1}$ or higher.

(9) an anti-Fas ligand antibody according to any one of (1) to (7) which binds to human Fas ligand with an affinity constant of at least $10^7 M^{-1}$, preferably $10^8 M^{-1}$, more preferably $10^9 M^{-1}$ and especially $10^{10} M^{-1}$ or higher.

(10) an anti-Fas ligand antibody which comprises at least one, preferably all of complementarity determining regions (CDRs) shown in FIG. 10 or FIG. 11.

(11) an anti-Fas ligand antibody according to any one of (1) to (9) which comprises at least one, preferably all of complementarity determining regions (CDRs) shown in FIG. 10 or FIG. 11.

(12) a humanized immunoglobulin (Ig) comprising at least one, preferably all of framework regions (FR) from a human acceptor Ig and at least one, preferably all of CDRs from a non-human donor Ig which specifically binds to human Fas ligand.

(13) a humanized immunoglobulin (Ig) according to (12) which suppresses Fas ligand-induced apoptosis of Fas antigen-expressing cells.

(14) a humanized immunoglobulin (Ig) according to (12) wherein said non-human donor Ig is mouse F919-9-18 monoclonal antibody.

The term, neutralizing antibody used herein designates an antibody exhibiting the activity of suppressing the Fas ligand-induced apoptosis of the Fas antigen-expressing cells, which exhibits the level of the apoptosis (expressed in terms of radioactivity or specific lysis (%)) measured by the method described in the Examples 1 to 3 or by a known method lower than the level of the control group such as the group with no antibody addition. More illustratively, a neutralizing antibody is an antibody exhibiting an apoptosis suppression calculated by the following equation of 10% or higher, preferably 30% or higher, and more preferably 50% or higher, and most preferably 90% or higher.

Apoptosis suppression rate (%)

$$\frac{\left(\begin{array}{c}\text{Radioactivity of}\\\text{the control group}\end{array} - \begin{array}{c}\text{Radioactivity of the}\\\text{antibody-added group}\end{array}\right)}{\text{Radioactivity of the control group}} \times 100$$

The term, biological activity of the Fas ligand designates the activity of the Fas ligand to induce or suppress the apoptosis of the Fas antigen-expressing cells, which may be measured by the method described in Examples 1 to 3 as will be described, or alternatively, by a known method.

The term, anti-Fas ligand antibody designates an antibody that has an activity to react with the Fas ligand, and includes the antibody whose binding with the antigen Fas ligand (for example, the extracellular domain of the Fas ligand) may be confirmed by any of the method described in the present specification or by a known method.

This invention also provides,

[2] An anti-Fas ligand antibody against a particular peptide derived from the Fas ligand.

(1) An anti-Fas ligand antibody which specifically reacts with said peptide.

(2) An anti-Fas ligand antibody according to (1) wherein said peptide is a peptide selected from SEQ ID Nos. 1 to 8.

(3) An anti-Fas ligand antibody according to (1) wherein said peptide is the peptide of SEQ ID No. 1 or 6.

(4) An anti-Fas ligand antibody according to (1) wherein said peptide is the peptide of SEQ ID No. 1.

(5) An anti-Fas ligand antibody according to (4) wherein said peptide is the peptide of the region corresponding to the amino acid Nos. 1 to 9, or 10 to 18 described in the amino acid sequence of SEQ ID No. 1.

The antibody of the present invention [1] is an antibody that recognizes the epitope critical for the expression of the biological activity of the Fas ligand. Such an epitope is believed to be the epitope that is expressed in the biologically active Fas ligand, for example, the extracellular domain of the Fas ligand; free Fas ligand; polypeptides nd5, nd12, nd20, nd32 and nd42 which are the deletion mutants of the extracellular domain of the Fas ligand; and L179F which is a substitution mutant of the extracellular domain of the human Fas ligand, but that is not expressed in the biologically inactive Fas ligands, for example, polypeptide nd49 which is the deletion mutant of the extracellular domain of the Fas ligand; polypeptide cd179 which is the deletion mutant of the extracellular domain of the human Fas ligand; an aggregate of the extracellular domain of the Fas ligand formed by salting out with ammonium sulfate described in Examples 4-1.

This invention also provides antibodies which have binding affinities to human Fas ligand under standard binding conditions (e.g., physiological saline or serum conditions) in an assay described later in [Examples] of at least about $10^7 M^{-1}$, and preferably $10^8 M^{-1}$ to $10^{10} M^{-1}$ or stronger, and provides antibodies which comprises at least one, preferably all of complementarity determining regions (CDRs) shown in FIG. 10 or FIG. 11.

The preferred embodiments of the antibodies of the present invention [1] include the monoclonal antibody produced by hybridoma F919-9-18; an antibody which recognizes the epitope identical with the one recognized by such monoclonal antibody; and an antibody which competes with such monoclonal antibody for binding with the corresponding antibody. The antibody of the present invention [1] is capable of suppressing the apoptosis to a high degree. The antibody of the present invention [1] can also be used in an assay method wherein a Fas ligand, in particular, a biologically active Fas ligand in human body fluid is detected at a high sensitivity.

Preferred embodiments of the antibody of the present invention [2] include monoclonal antibodies produced by hybridomas F918-7-3, F918-9-4 and the like; an antibody which recognizes the epitope identical with the one recognized by such monoclonal antibody; and an antibody which competes with such monoclonal antibody for binding with the corresponding antibody. The antibodies of the present invention [2] specifically react with the Fas ligand, and with the Fas ligand of particular species whose region involved in the reaction has been clearly found out. Therefore, such an antibody can be used in a high sensitivity assay of a Fas ligand in human body fluid. Such an antibody can also be used in the assay wherein one or more particular Fas ligand is selectively detected.

The anti-Fas ligand antibody of the present invention may be a monoclonal antibody or a polyclonal antibody so long as it binds to the Fas ligand or a peptide derived from the Fas ligand. Use of a monoclonal antibody, however, is more preferable in view of the clear properties.

An antibody, namely an immunoglobulin comprises H chain and L chain, and belongs to one of the 5 classes (IgG, IgA, IgM, IgD, and IgE) on the bases of its physicochemical and immunological characteristics. Among these classes, IgG and IgA are further divided into subclasses on the bases of their H chain types. The anti-Fas ligand antibody of the present invention may belong to any of such classes and subclasses.

The immunoglobulin is divided into two fragments, $F(ab')_2$ and Fc' when digested with pepsin, and into Fab and Fc when digested with papain. The antibody of the present invention may be either a complete antibody or a fragment constituting a part of the antibody. The antibody of the present invention may also be a chimeric antibody.

The basic antibody structural unit is known to comprise a tetramer. Each tetramer is composed of two identical pairs of polypeptide chains, each pair having one "light" (about 25 KD) and one "heavy" chain (about 50–70 KD). The NH2-terminus of each chain begins a variable region of about 100 to 110 or more amino acids primarily responsible for antigen recognition. The COOH part of each chin defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See, generally, Fundamental Immunology, Paul, W., Ed., Chapter 7, Pgs. 131–166, Raven Press, N.Y. (1984), Which is incorporated herein by reference.)

The variable regions of each light/heavy chain pair form the antibody binding site. The chains all exhibit the same general structure of relatively conserved framework regions joined by three hypervariable regions, also called Complementarity Determining Regions or CDRs (see, "sequences of Proteins of Immunological Interest," Kabat, E., et al., U.S. Department of Health and Human Services, (1987); and Chothia and Lesk, J. Mol. Biol., 196, 901–917 (1987), which are incorporated herein by reference). The CDRs from the two chains of each pair are aligned by the framework regions, enabling binding to a specific epitope.

As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. The immunoglobulins may exist in a variety of forms besides antibodies; including, for example, Fv, Fab, and $(Fab')_2$ as well as bifunctional hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879–5883 (1988) and Bird et al., Science, 242, 423–426 (1988), which are incorporated herein by reference) (See, generally, Hood et al., Immunology, Benjamin, N.Y., 2nd ed. (1984), Harlow an d Lane , Antibodies. A Laboratory Manual, Cold Spring Harbor Laboratory (1988) and Hunkapiller and Hood, Nature, 323, 15–16 (1986), which are incorporated herein by reference).

It is well known that native forms of "mature" immunoglobulins will vary somewhat in terms of length by deletions, substitutions, insertions or additions of one or more amino acids in the sequences. Thus, both the variable and constant regions are subject to substantial natural modification, yet are "substantially identical" and still capable of retaining their respective activities. Human constant region and rearranged variable region DNA sequences can be isolated in accordance with well known procedures from a variety of human cells, but preferably immortalized B-cells. Similar methods can be used to isolate non-human immunoglobulin sequences from non-human sources. Suitable source cells for the DNA sequences and host cells for expression and secretion can be obtained from a number of sources, such as the American Type Culture Collection ("Catalogue of Cell Lines and Hybridomas," Fifth edition (1985) Rockville, Md., U.S.A., which is incorporated herein by reference).

In addition to these naturally-cocurring forms of immunoglobulin chains, "substantially identical" modified heavy and light chains can be readily de signed and manufactured utilizing various recombinant DNA techniques well known to those skilled in the art. For example, the chains can vary from the naturally-occurring sequence at the primary structure level by several amino acid substitutions, terminal and intermediate additions and deletions, and the like. Alternatively, polypeptide fragments comprising only a portion of the primary structure may be produced, which fragments possess one or more immunoglobulin activities (e.g., binding activity). In particular, it is noted that like many genes, the immunoglobulin-related genes contain separate functional regions, each having one or more distinct biological activities. In general, modifications of the genes encoding the desired epitope binding components may be readily accomplished by a variety of well-known techniques, such as site-directed mutagenesis (see, Gillman and Smith, Gene 8:81–97 (1979) and Roberts, S. et all., Nature 328:731–734 (1987), both of which are incorporated herein by reference). In preferred embodiments of the invention, the epitope binding component is encoded by immunoglobulin genes that are "chimeric" or alternatively "humanized" (see, generally, Co and Queen (1991) Nature 351:501, which is incorporated herein by reference).

Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $\gamma_1$ and $\gamma_4$. A typical therapeutic chimeric antibody is thus a hybrid protein consisting of the V or antigen-binding domain from a mouse antibody and the C or effector domain from a human antibody, although other mammalian species may be used.

As used herein, the term "framework region" refers to those portions of immunoglobulin light and heavy chain variable regions that are relatively conserved (i.e., other than the CDRs) among different immunoglobulins in a single species, as defined by kabat, et al., op.cit. As used herein, a "human framework region" is a framework region that is substantially identical (about 85% or more) to the framework region of a naturally occurring human antibody.

As used herein, the term "humanized immunoglobulin" refers to an immunoglobulin comprising a human framework, at least one, preferably all of CDRs from a non-human antibody, and in which any constant region present is substantially identical to a human immunoglobulin constant region, i.e., at least about 85–90%, preferably at least 95% identical. Hence, all parts of a humanized immunoglobulin, except possibly the CDRs, are substantially identical to corresponding parts of one or more native human immunoglobulin sequences. For example, a humanized immunoglobulin would not encompass a chimeric mouse variable region/human constant region antibody.

As a more preferred mode of the present invention, an anti-Fas ligand antibodies which is humanized immunoglobulin specifically reactive with Fas ligand is also provided. More specifically this invention provides an anti-Fas ligand antibody according to any one of antibodies of the invention [1] which is a humanized immunoglobulin (Ig) comprising human acceptor framework regions (FRs) and CDRs from the non-human, preferably rodent and more preferably mouse donor Ig which specifically binds to human Fas ligand. The immunoglobulins can have two pairs of light chain/heavy chain complexes, at least one chain comprising one or more donor(mouse) CDRs, with or without additional naturally-associated donor(mouse) amino acid residues, can be introduced into human framework regions to pro duce humanized immunoglobulins capable of binding to Fas ligand at affinity levels stronger than about $10^7$ $M^{-1}$. These humanized immunoglobulins will also be capable of blocking the binding of the CDR-donating mouse monoclonal antibody to Fas ligand. In a preferred embodiment, one or more of the CDRs will come from the F919-9-18 antibody, and the humanized immunoglobulin will be of the IgG1 or IgG4 isotype.

More definitely, the humanized immunoglobulin of this invention comprises at least one, preferably all of CDRs each comprising or consisting of the amino acid sequence of SEQ ID Nos. 11, 13, 15, 19, 21, or 23.

Generally, the humanized antibodies of the invention will comprise heavy chain variable region sequences wherein the sequence of the humanized immunoglobulin heavy chain variable region framework is more than 65% identical but less than 95% identical to the sequence of the donor immunoglobulin heavy chain variable region framework, preferably the variable region framework is more than 70% identical to the sequence of the donor immunoglobulin.

As to the human framework region, a framework or variable region amino acid sequence of a CDR-providing non-human immunoglobulin is compared with corresponding sequence in a human immunoglobulin sequence collection, and a sequence having high homology is selected.

Preferably, the sequence of the acceptor immunoglobulin heavy chain variable region is among the 5, more preferably 3 sequences in a representative collection of sequences of human immunoglobulin heavy chain variable regions most homologous to the sequence of the donor immunoglobulin heavy chain variable region. The design of humanized immunoglobulins may be carried out as follows. (1) When an amino acid falls under the following category, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulin at that position, whereas the corresponding amino acid in the donor immunoglobulin is typical for human immunoglobulin at that position;

(b) the position of the amino acid is immediately adjacent to one of the CDR's; or (c) at least one atom of the amino acid is within about 5 A, preferably 4 A, more preferably 3 A of a CDR in a tertiary structure immunoglobulin model (see, Queen et al., op. cit., and Co et al., Proc, Natl. Acad. Sci. USA, 88, 2869 (1991), respectively, both of which are incorporated herein by reference.).

(2) When each of the amino acid in the human framework region of the acceptor immunoglobulin and a corresponding amino acid in the donor immunoglobulin is unusual for human immunoglobulin at that position, such an amino acid is replaced by an amino acid typical for human framework region at that position. For a detailed description of the production of humanized immunoglobulins (see, Queen et al. (op. cit.) and Co et al. (op. cit.)).

In general, substitution of all or most of the amino acids fulfilling the above criteria is desirable.

More definitely, the humanized antibody of the present invention will usually contain a substitution of a human light chain framework residue with a corresponding donor (mouse) framework residue in at least 1, 3, 5, and more usually 7 of the positions shown in Tables 4 and 5. The humanized antibodies also usually contain a substitution with a corresponding donor (mouse) heavy chain framework residue in at least 1, 3, 5, 7, 9, 11, 13 and, more usually 16 of the positions shown in Tables 4 and 5.

Humanized antibodies have at least three potential advantages over mouse and in some cases chimeric antibodies for use in human therapy:

1) because the effector portion is human, it may interact better with the other parts of the human immune system (e.q., destroy the target cells more efficiently by complement-dependent cytotoxicity (CDC) or antibody-dependent cellular cytotoxicity (ADCC).

2) The human immune system should not recognize the framework or C region of the humanized antibody as foreign, and therefore the antibody response against such an injected antibody should be less than against a totally foreign mouse antibody or a partially foreign chimeric antibody.

3) Injected mouse antibodies have been reported to have a half-life in the human circulation much shorter than the half-life of normal antibodies (Shaw, D. et al., J.

Immunol. 138,4534–4538 (1987)). Injected humanized antibodies will presumably have a half-life more like that of naturally occurring human antibodies, allowing smaller and less frequent doses to be given.

The anti-Fas ligand antibodies of the present invention include both the one that affects and that does not affect the binding of the Fas antigen and the Fas ligand. The antibody such as the anti-Fas ligand antibody of the present invention [1] that binds to the Fas ligand without inducing the apoptosis may be used as a substance that competes with the Fas ligand in the body for the purpose of artificially suppressing the apoptosis. The anti-Fas ligand antibodies of the present invention may be used for the assay of the Fas ligand, and as a component of the reagent or kit for such an assay.

The present invention also provides an assay method as described below.

[3] A method for assaying a Fas ligand in human body fluid using an anti-Fas ligand antibody.

(1) A method for assaying a Fas ligand wherein at least one of the antibodies described in [1] or [2] is used.

(2) The method according to (1) carried out by competitive method.

(3) The method according to (1) carried out by sandwich method.

(4) The method according to (1) to (3) wherein two or more neutralizing antibodies of the same or different types are used in combination.

(5) The method according to (1) to (3) wherein two or more antibodies of the same or different types according to [2] are used in combination.

(6) The method according to (1) to (3) wherein the neutralizing antibody and the antibody according to [2] are used in combination.

The neutralizing antibody, and in particular, the neutralizing antibody of the present invention is believed to recognize a structure or an epitope on the Fas ligand that is necessary for the biological activity of the Fas ligand, and therefore, the assay method of the present invention utilizing the neutralizing antibody is capable of detecting the Fas ligand, and in particular, a biologically active Fas ligand in the specimen, and in particular, the human body fluid at a high sensitivity. The assay method may be used as a substitute for a bioassay wherein biological activity of the Fas ligand in the specimen is measured. As described above, the Fas ligand has been indicated to exist and function under physiological conditions as a trimer, and an assay by sandwich method may be carried out by using the same antibody in combination as will be described in the Examples.

Since the antibodies of the present invention [2] specifically react with the Fas ligand, and the peptide region involved in such reaction has been clearly found out, the assay method utilizing the antibody of the present invention [2] is capable of assaying the Fas ligand in the specimen, and in particular, human body fluid at a high sensitivity. A selective assay of one or more particular Fas ligand is also possible.

By combining the neutralizing antibody, especially the neutralizing antibody of the present invention with the antibody of the present invention [2], a selective assay of one or more particular biologically active Fas ligand would be possible.

Furthermore, simultaneous evaluation of the same specimen by different assay methods of the present invention would enable the measurement of the total amount of the Fas ligand, the amount of the particular Fas ligand, and ratio in the amount of the particular Fas ligands. Such evaluation would enable the measurement of not only the quantitative fluctuation but also the qualitative fluctuation of the Fas ligand in a particular disease or disease conditions.

The sample assayed by the present invention is not limited to any particular type. The assay method of the present invention, however, is adapted for evaluation of the Fas ligand in human body fluids, and the preferable human body fluid samples are the one selected from blood, plasma, serum, urine, spinal fluid, lymph, saliva, ascites, and pleural fluid.

As shown in the Examples, the Fas ligand which is the antigen recognized by the antibody of the present invention, and which is the substance detected in the assay method of the present invention is not limited to any particular Fas ligand so long as it is derived from human Fas ligand. The Fas ligand may be the one that binds to, or that does not bind to the Fas antigen; the one that induces or that does not induce the apoptosis; an endogenous Fas ligand inherently found in the organism or an exogenous Fas ligand; the one derived from natural organism or produced by genetic engineering means or chemical synthesis; or the one modified or unmodified with a sugar chain. Exemplary Fas ligands include, a Fas ligand-expressing cell, a Fas ligand, extracellular domain of the Fas ligand, a free Fas ligand or a peptide fragment derived from the Fas ligand, a deletion or substitution mutant Fas ligand wherein one or more amino acid is deleted or substituted, and a fusion protein including a part of the Fas ligand.

The present assay method may be used for assaying the Fas ligand in the body fluids of normal donors or those suffering from various diseases. It should be also noted that it is the present invention that has for the first time enabled to find out the concentration of the Fas ligand in the body fluid. For example, those suffering from hepatitis, HIV infections, or an autoimmune disease exhibit a Fas ligand concentration higher than normal donors, and such findings may be utilized in the diagnosis of such diseases.

The present invention further provides a method as described below.

[4] A method for assaying a Fas ligand in human body fluid using an anti-Fas ligand antibody.

(1) A method for assaying a Fas ligand in human body fluid used for prediction or detection of an increase/decrease of the Fas ligand and/or an abnormality of Fas antigen/Fas ligand system; and prediction, detection and diagnosis of the disease involving such abnormality and pathological conditions associated with such disease.

(2) A method for detecting systemic or topical pathological conditions caused by the abnormality of Fas/Fas ligand system in a disease involving the abnormality of the Fas/Fas ligand.

(3) The method according to (1) or (2) carried out by the method according to [3].

(4) The method according to (1) to (3) wherein said disease is an autoimmune disease, hepatitis, or HIV infection.

The present invention further provides a hybridoma as described below.

[5] A hybridoma or a cell line producing an anti-Fas ligand antibody.

(1) A hybridoma or a cell line producing the antibody according to [1] or [2].

(2) A hybridoma with accession No. FERM P-15000 (FERM BP-5533), FERM P-15001(FERM BP-5534), or FERM P-15002 (FERM BP-5535). These three hybridomas have been deposited under the conditions of the Budapest Treaty.

Furthermore the present invention also provides novel compositions or medicaments containing as an active ingredient at least any one of afore-mentioned anti-Fas ligand antibodies of the invention, and methods of treating systemic or topical pathological conditions or a disease with, caused by or involving the abnormality of Fas/Fas ligand system or of apoptosis through Fas antigen. The methods comprise a step administering at least any one of antibodies of the invention.

The process for obtaining the anti-Fas ligand antibody according to the present invention is further described in the following.

As shown in the Examples, the antigen used for producing the anti-Fas ligand antibody is not limited to any particular antigen so long as it contains the peptides derived from the Fas ligand. The antigen used for producing the anti-Fas ligand antibody of the present invention may be the one that binds to, or that does not bind to the Fas antigen; the one that induces or that does not induce the apoptosis; the one derived from natural organism or produced by genetic engineering means or chemical synthesis; or the one modified or unmodified with a sugar chain. Exemplary antigens include a Fas ligand-expressing cell, the Fas ligand in its full length, the extracellular domain of the Fas ligand, a free Fas ligand, a peptide fragment derived from the Fas ligand, a deletion or substitution mutant of the Fas ligand wherein one or more amino acid has been deleted or substituted, and a fusion protein including a part of the Fas ligand.

The anti-Fas ligand antibody of the present invention, which may be a monoclonal or a polyclonal antibody, may be produced by referring to known procedures (see, for example, "Manipulations in Immunology Experiments (in Japanese)", edited an issued by Society of Immunology, Japan). The production of the anti-Fas ligand antibody is briefly described.

To produce the anti-Fas ligand antibody, an animal is first inoculated with an immunizing antigen (Fas ligand or a peptide which is a part of the Fas ligand) and an optional adequate adjuvant such as complete Freund's adjuvant (FCA) and incomplete Freund's adjuvant (FIA), and if necessary, the animal is additionally immunized at an interval of two to four weeks. After the additional immunization, blood is collected to obtain the anti-serum. The Fas ligand used for the antigen is not limited in terms of its production process, so long as the Fas ligand used has a purity sufficient for the production of the antibody.

When the polypeptide used for the immunization antigen is a low molecular weight polypeptide comprising about 10 to 20 amino acids, the polypeptide may be bound to a carrier such as keyhole lympet hemocyanine (KLH) before its use for the antigen. The animal immunized with the Fas ligand is not limited to any particular species, and the preferred are the animals commonly used by those skilled in the art for immunological experiments such as rat, mouse, rabbit, hamster, sheep, horse, hen, goat, pig and cow. It is preferable to select an animal species capable of producing the antibody of interest.

A polyclonal antibody may be produced by purifying the resulting anti-serum. The purification may be carried out by the combination of salting out, ion exchange chromatography, affinity chromatography, and other adequate procedures.

A monoclonal antibody may be produced as described below. Antibody-producing cells such as splenocytes or lymphocytes are collected from the immunized animal, and the collected cell is fused with a myeloma cell line by the procedures utilizing polyethylene glycol, Sendai virus, electric pulse, or the like to prepare a hybridoma. A clone producing a Fas ligand-binding antibody is then selected, and cultivated. The monoclonal antibody is obtained by purifying the supernatant of the selected clone. The purification may be carried out by the combination of salting out, ion exchange chromatography, affinity chromatography, and other adequate procedures.

The anti-Fas ligand antibody may also be obtained by a genetic engineering process. For example, a mRNA may be collected from the splenocyte or lymphocyte of the animal immunized with the Fas ligand or its peptide fragment, or from the hybridoma producing the monoclonal antibody against the Fas ligand, and a cDNA library may be prepared by using the thus collected mRNA. A clone producing the antibody that is reactive with the antigen is screened, and the thus obtained clone is cultivated. The antibody of interest is then obtained from the culture mixture, and purified by the combination of known procedures.

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementarity determining regions can be produced synthetically or by combining appropriate cDNA and genomic DNA segments.

In one aspect, the present invention is directed to recombinant DNA segments encoding the heavy and/or light chain CDRs from an immunoglobulin capable of binding to a desired epitope of Fas ligand, such as monoclonal antibody F919-9-18. The DNA segments encoding these regions will typically be joined to DNA segments encoding appropriate human framework regions. Exemplary DNA sequences, which on expression code for the polypeptide chains comprising the heavy and light chain CDRs of monoclonal antibody F919-9-18 are included in FIGS. 12 and 13. Due to codon degeneracy and non-critical amino-acid substitutions, other DNA sequences can be readily substituted for those sequences, as detailed below. For a detailed description of the design and production of humanized immunoglobulins, see, commonly assigned Ser. Nos. 07/290,975 and 07/310, 252, filed Dec. 28, 1988 and Feb. 13, 1989, respectively, and International Patent Application Laid-Open No. WO90/07861, both of which are incorporated herein by reference.

The DNA segments will typically further include an expression control DNA sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the light chains, heavy chains, light/heavy chain dimers or intact antibodies, binding fragments or other immunoglobulin forms may follow.

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and Cregions), as well as by a variety of different techniques. Joining appropriate genomic and synthetic sequences is presently the most common method of production, but cDNA sequences may also be utilized (see, European Patent Publication No. 0239400 and Reichmann, L. et al., Nature 332, 323–327 (1988), both of which are incorporated herein by reference).

Human constant region DNA sequences can be isolated in accordance with well known procedures from a variety of human cells, but preferably immortalized B-cells (see, Kabat op. cit. and WP87/02671). The CDRs for producing the immunoglobulins of the present invention will be similarly derived from monoclonal antibodies capable of binding to Fas ligand and produced in any convenient mammalian source, including, mice, rats, rabbits, or ther vertebrate capable of producing antibodies by well known methods. Suitable source cells for the DNA sequences and host cells for immunoglobulin expression and secretion can be obtained from a number of sources, such as the American Type Culture Collection (Catalogue of cell Lines and Hybridomas, Fifth edition (1985) Rockville, Md., U.S.A., which is incorporated herein by reference). In preferred embodiments, the CDRs have sequences corresponding to the CDR sequences of F919-9-18, and may include degenerate nucleotide sequences encoding the corresponding CDR amino acid sequence(s) of F919-9-18.

In addition to the humanized immunoglobulins specifically described herein, other "substantially homologous" modified immunoglobulins can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, Gene 8,81–97 (1979) and Roberts S. et al, Nature 328,731–734 (1987), both of which are incorporated herein by reference).

Alternatively, polypeptide fragments comprising only a portion of the primary antibody structure may be produced, which fragments possess one or more immunoglobulin activities (e.g., binding activity). These polypeptide fragments may be produced by proteolytic cleavage of intact antibodies by methods well known in the art, or by inserting stop codons at the desired locations in the vectors pvk and pvgl (Co et al., J. Immunol. 148, 1149 (1992)) using site-directed mutagenesis, such as after CH1 to produce Fab fragments or after the hinge region to produce (Fab')2 fragments. Single chain antibodies may be produced by joining VL and VH with a DNA linker (see Huston et al., opcit., and Bird et al., op cit.). As one example, Fv or Fab fragments may be produced in E. coli according to the methods of Buchner and Rudolph (1991) Bio/Technology 9:157–162 and Skerra et al. (1991) Bio/Technology 9:273–277, incorporated herein by reference). Fv and Fab may also be produced by expression of encoding polynucleotides in eukaryotic, preferably mammalian, cells. Also because like many genes, the immunoglobulin-related genes contain separate functional regions, each having one or more distinct biological activities, the genes may be fused to functional regions from other genes (e.g., enzymes, see, commonly assigned U.S. Ser. No. 132,387, filed Dec. 15, 1987, which is incorporated herein by reference) to produce fusion proteins (e.g., immunotoxins) having novel properties.

The anti-Fas ligand antibody of the present invention may be used for detecting the Fas ligand in body fluids and tissues. Also, the anti-Fas ligand antibody of the present invention may be used for preparing an antibody column adapted for use in the preparation of the Fas ligand, and for detecting the Fas ligand of the present invention in the fractions obtained in course of the purification.

The anti-Fas ligand antibodies of the present invention include the antibodies that modify, namely, promote or suppress the action of the Fas ligand to the cell.

To obtain the antibody that has the effect of suppressing the Fas ligand-induced apoptosis, the serum produced in the course of producing the above-described monoclonal antibody or polyclonal antibody, or the supernatant of the hybridoma is screened by an in vitro assay utilizing the Fas ligand or the Fas ligand-expressing cell, and the Fas antigen-expressing cell. The antibody of interest is purified from the serum or the supernatant selected in such screening by an adequate combination of known methods. The preferred embodiments of the screening process utilizing the Fas ligand or the Fas ligand-expressing cell and the Fas antigen-expressing cell are shown in the Examples, and it should be noted that such screening process is also described in International Patent Application Laid-Open No. 95/13293 and the like. The screening may also be carried out by using reactivity or non-reactivity with a particular Fas ligand shown in the Examples for the index, namely by using the reactivity with at least one of nd32, nd42, and L179F, or the non-reactivity with at least one of nd42 and cd179 for the index.

The neutralizing antibodies of the present invention that are capable of suppressing the Fas ligand-induced apoptosis to a high degree may be used for the purpose of regulating the apoptosis in the body. For example, the neutralizing antibody may be used as a therapeutic agent in treating diseases wherein apoptosis of the cells and tissues are involved, for example, destruction of articular tissue in rheumatism, destruction of autotissue in systemic lupus erythematosu (SLE), diabetes, influenza, AIDS, hepatitis and the like.

On the other hand, the antibodies of the present invention that promote the Fas ligand-induced apoptosis may be used for the removal of the cells that are unnecessary for the body in the treatment of, for example, early phase AIDS, abnormal propagation of synovial membrane cells in rheumatism, and propagation of autoantigen-reactive T cells in autoimmune diseases.

Use of the Fas ligand itself for the treatment and the research should require a production of the Fas ligand protein of high purity in a large quantity. The anti-Fas ligand antibody of the present invention is useful for the purification of the Fas ligand. The anti-Fas ligand antibody of the present invention selectively binds to the biologically active Fas ligand, and therefore, the anti-Fas ligand antibody of the present invention is particularly useful for a specific, high-efficiency purification of the active Fas ligand which should serve an important therapeutic reagent.

The assay method of the present invention comprises the step wherein the antibody obtained as described above is employed, and such step may preferably be the step wherein the analyte in the test sample is trapped by an antigen-antibody reaction between the analyte Fas ligand in the test sample and the antibody obtained as described above.

The principle by which the analyte substance is detected in the assay method of the present invention is not limited to any particular principle. Exemplary principles, however, include aggregation method, sandwich method, solid phase direct method, and competitive method. Among these, the preferred are the sandwich method and the competitive method, and the most preferred is the sandwich method.

In the aggregation method, the antibody is allowed to bind to the surface of a particle such as latex particle and erythrocyte (for example, sheep erythrocyte) so that an aggregation of the particles would take place when the Fas ligand is present, and the Fas ligand is measured by using the degree of the aggregation for the index.

It should be noted that, in the aggregation method, particles commonly used in the art such as gelatin particles, microbeads, and carbon particles can be used in addition to the latex and the erythrocyte.

In the sandwich method, the solid phase direct method, and the competitive method, the assay may be carried out with a labeled antigen and/or antibody by adopting the principles such as enzyme immunoassay (EIA), radioimmunoassay (RIA), chemiluminescence immunoassay, fluoroimmunoassay, time-resolved fluoroimmunoassay (TR-FIA), and immunochromatographic assay (ICA).

Next, the solid phase sandwich method, the solid phase direct method, and the solid phase competitive method carried out by adopting the principle of EIA, which is one of the preferable assay principles of the present invention, are described.

In the solid phase sandwich method by the EIA, a Fas ligand-recognizing antibody labeled with an enzyme such as peroxidase, alkaline phosphatase, or β-galactosidase is first prepared, and a Fas ligand-recognizing antibody is adsorbed on the solid phase employed. After the addition of the sample or the standard, the enzyme-labeled antibody as described above is added to start the antigen-antibody reaction. After washing off the excessive enzyme-labeled antibody, a chromogenic substrate adequate for the enzyme employed, for example, o-phenylenediamine and $H_2O_2$, p-nitrophenyl phosphate, 2-nitrophenyl-β-D-galactoside is added to start the reaction with the enzyme. The color development of the substrate depends on the amount of the enzyme, and hence on the amount of the Fas ligand in the sample. Accordingly, the Fas ligand can be quantitated by measuring the amount of the final color-developed product.

In the solid phase direct method, the s ample is directly adsorbed onto the solid phase, and the surface of the solid phase that does not absorb th e Fas ligand is blocked with a protein such as BSA (bovine serum albumin) that does not affect the measurement. An enzyme-labeled antibody that recognizes the Fas ligand is then added to start the reaction. The manipulations similar to those of the solid phase sandwich method are subsequently conducted to determine the presence/absence of the Fas ligand in the sample, or to quantitate the Fas ligand in the sample.

In the solid phase competitive method, the Fas ligand of a particular amount recognizable by the antibody employed is directly adsorbed onto the solid phase, and the solid phase is then blocked. An enzyme-labeled antibody that recognizes the Fas ligand and the test sample are then added, and the reaction is allowed to take place for a certain period of time. The substances that failed to bind to the solid phase are then washed off, and a chromogenic substrate is added for reaction with the enzyme. After the completion of the reaction, degree of inhibition of the binding of the enzyme-labeled antibody to the Fas ligand on the solid phase by the addition of the sample is measured to quantitate the Fas ligand in the sample.

In the same manner, after the adsorption of the antibody onto the solid phase, the enzyme-labeled Fas ligand and the sample may be simultaneously added to measure the degree of inhibition of the binding of the enzyme-labeled Fas ligand to the solid phase-immobilized antibody by the addition of the sample, and hence, to quantitate the Fas ligand in the sample.

In addition to the assay methods as described above, the Fas ligand may be measured by carrying out the antigen-antibody reaction in a liquid phase, and subsequently separating the Fas ligand that became bound to the labeled antibody from the Fas ligand that failed to bind to the labeled antibody by aggregation precipitation method utilizing the antibody or by other physicochemical method for quantification of the Fas ligand. The Fas ligand may also be measured by obtaining and labeling a secondary antibody that recognizes the Fas ligand-recognizing antibody, and subjecting it to the antigen-antibody reaction to thereby measure the Fas ligand, instead of labeling the Fas ligand-recognizing antibody.

In any of the sandwich method, the solid phase direct method, and the competitive method, the combination of the labeled enzyme and the chromogenic substrate may be replaced with the combination of the labeled enzyme and a bioluminescent or chemiluminescent substrate, or the labeled enzyme and a fluoroluminescent substrate. Typical enzyme-luminescent substrate combinations that may be employed in such a case include alkaline phosphatase-AMPPD, horse radish peroxidase-luminol, and luciferase-luciferin, and typical enzyme-fluoroluminescent substrate combinations include alkaline phosphatase-umbelliferyl phosphate, and horseradish peroxidase-p-hydroxyphenyl propionate.

In the three assay methods as described above, an antibody or an antigen directly or indirectly labeled with a radioisotope, a chemiluminescent substance, or a fluorescent substance may be used instead of the enzyme to measure the Fas ligand in the sample by means of determining the intensity of the radioactivity, luminescence, or fluorescence.

Exemplary radioisotopes commonly used in such case include $^{125}I$ and $^{131}I$. Typical chemiluminescent substances include acridinium ester. When fluorescent intensity is measured, a method of higher sensitivity may be adopted wherein a chelating agent is directly or indirectly bonded to the antibody or the antigen, and an excitation beam is irradiated to measure the intensity of the fluorescence emitted from the rare earth metal bonded to the chelating agent in a time-resolusive manner to thereby measure the Fas ligand in the sample (time-resolved fluoroimmunoassay, TR-FIA). Typical rare earth metals include europium.

As described above, the purpose of the assay method of the present invention is the measurement of the Fas ligand in the sample. The test sample may be a body fluid or an extract or supernatant of a tissue, cells, or mycelium, and may preferably be a body fluid. More preferably, the test sample may be a sample selected from blood, plasma, serum, urine, spinal fluid, lymph, saliva, ascites, and pleural fluid.

The assay method of the present invention may be used for the assay of the Fas ligand in the body fluid of normal donors or those suffering from various diseases. The present invention has for the first time enabled the measurement of the Fas ligand concentration in the body fluid, and demonstrated the fluctuation of the Fas ligand concentration in some particular diseases.

EXAMPLES

Next, the present invention is more illustratively described by referring to Examples, which are merely given for illustration purpose and which by no means limit the scope of the invention.

The abbreviations used in the following description are those based on the abbreviations commonly used in the field of the art.

The manipulations used in the Examples as described below has been carried out by referring to Sambrook et al. ed., "Molecular Cloning, a Laboratory Manual, 2nd ed.", Cold Spring Harbor Laboratory, 1989; Imamoto, F. et al. ed., "Introduction of Recombinant Gene into Cell and the Expression (In Japanese)", Tanpakushitsu-Kakusan-Kouso (Protein, Nucleic acid and Enzyme), Special Issue 28(14), 1983; and Okada, Y. (supervision), "Cell Engineering Technology (Summary of Serial Articles) (in Japanese)", Jikken-Igaku (Experimental Medicine), Special Issue 7(13), 1989; and the like.

1. Preparation of anti-Fas ligand peptide antibody 1-1 Selection of antigen peptide As shown in FIG. 1, the predicted epitope in the extracellular domain of the Fas ligand of SEQ ID No. 9 in the Sequence Listing was analyzed. A data base of an archive of experimentally determined three-dimensional structures of biological macromolecules, PROTEIN DATA BANK (PDB) was searched with FASTA program included in the Homology module of BIOSYM INC. for a protein having a high homology with the amino acid sequence in the extracellular domain of the Fas ligand. It was then found that TNF-α (PDB-ID 1TNF and 2TUN) was highly homologous in their entire structure. Modeling of the extracellular domain of the Fas ligand was then conducted by using such TNF-α three-dimensional structures for the reference proteins. In the construction of the model structure, extraction of the structure conserved region (SCR) that is used for the basic structure was carried out by overlaying the monomer structures of the TNF-α at the α carbon, and selecting the region wherein structural gap is within 1 Å, and the temperature factor in the X-ray crystal diffraction is up to 20. With regard to the variable region (VR) linked to the structure conserved region, PDB was searched for an adequate structure when insertion or deletion had occurred. Homology module of BIOSYMS INC. was used for the construction of the structure. Global minimum search of the conformation was conducted for the substituted side chain in the constructed initial structure, and structure optimization was conducted using the calculation software, Discover of BIOSYMS INC. to obtain the model structure of the extracellular domain of the Fas ligand. Using the thus obtained model structure, the structural region exposed on the molecule surface, the region that exhibits a large gap upon overlaying of the monomer structures of the TNF-α, and the region with a high TNF-α (temperature factor were selected as the regions including the epitopes that are easily recognized by the antigen. On the basis of the information on secondary structure of the model structure, 8 peptide sequences having the amino acid sequence shown in SEQ ID Nos. 1–8 of the Sequence Listing were selected to facilitate the maintenance of the antigen structure upon synthesis of the peptides of such regions. The amino acid sequences of the eight peptides selected are shown in FIG. 1. The synthetic peptides have cysteine containing SH group introduced in their C terminal for binding with the carrier. SEQ ID Nos. 1–8 in the Sequence Listing represent the sequences without such cysteine.

1-2 Preparation of antiserum

Based on the amino acid sequences shown in FIG. 1, peptides of SEQ ID Nos. 1–8 in the Sequence Listing were synthesized by entrusting the synthesis to Fujiya Bioscience Kenkyusho K.K. As shown in FIG. 1, the peptide Nos. corresponding to the amino acid sequences of SEQ ID Nos. 1–8 were designated M52–M59, and such designations are used in the following description. The binding to the carrier Keyhole Lympet hemocyanine (KLH) by maleimide method, and the immunization of the rabbit were entrusted to Men-eki Seibutsu Kenkyusho K.K.

1-3 Evaluation of antiserum

Increase in the antibody titer against the peptide administered was confirmed at Men-eki Seibutsu Kenkyusho K.K. by measuring the reactivity between the immobilized peptide and the antiserum. It was then found that the antiserums against the eight peptides administered react with the corresponding immobilized peptides at a dilution of about 6,000 to 24,000.

Next, western blotting was carried out to confirm the binding of the antiserum to the human Fas ligand.

A 10 μl portion of the culture supernatant containing the extracellular domain of the Fas ligand as will be described in 4-1 was mixed with an equal volume of gel loading buffer (SEPRASOL, Integrated Separation Systems), and incubated at 37° C. for 1 hour. To the wells of 4 to 20% SDS-PAGE (Tefco) was applied 2 μl of the solution, and the electrophoresis was allowed to take place at 25 mA and at room temperature for about 1 hour. After the completion of the electrophoresis, the gel was transferred to PDVF membrane (Millipore) under the conditions of 4° C. and 200 mA for 90 minutes. The membrane was blocked by immersing in a non-diluted blocking agent (BlockAce, Snow Brand Milk Products Co., Ltd.) at room temperature with shaking. The membrane was cut into lanes, and each lane was immersed in 1 ml of the antiserum diluted to 500 folds with 0.076M PBS, pH 6,4 containing 0.05% Tween 20 (hereinafter abbreviated as T-PBS) having 0.5% BSA added thereto, and shaken at room temperature for 1 hour. After the completion of the reaction, the lanes were washed twice with T-PBS, and then immersed in 1 ml of HRPO-labeled anti-rabbit Igs antibody (DACO) diluted to 500 folds with T-PBS having 10% goat serum added thereto, and the reaction was allowed to take place at room temperature for 1 hour. After washing the lanes for five times with T-PBS, detection was conducted with ECL system (Amersham).

Reactivity of the antiserum with the extracellular domain of the Fas ligand immobilized on a plate was confirmed by a plate assay (solid phase direct method).

First, 50 μl portions of the partially purified extracellular domain of the Fas ligand as will be described in 4-1 diluted to 0 to 25 ng/well with 0.076M PBS, pH 6.4 (hereinafter referred to as PBS) were dispensed in the wells of Immunoplate (Maxisorp, Nunc), and the Immunoplate was incubated at 45° C. for 30 minutes to immobilize the extracellular domain of the Fas ligand on the well. After washing the wells with ion exchange water for five times, 100 μl/well of 0.1% BSA/PBS was added to the wells for blocking of the well. After removing the blocking agent, the antiserum diluted with 0.1% BSA/PBS was added to the wells, and reacted at 37° C. for 1 hour. The wells were then washed twice with 0.9% NaCl containing 0.005% Tween 20, and 50 μl/well of HRPO-labeled anti-rabbit Igs antibody (DACO) diluted to 1,000 folds with 10% goat serum/PBS was added to the wells. The reaction was done at 37° C. for 1 hour. After the completion of the reaction, the wells were washed five times with the washing solution, and twice with ion exchange water, and 50 μl of 0.1M McIlvaine buffer (pH 5.0) containing 3 mg/ml o-phenylenediamine and 0.027% hydrogen peroxide was added to the wells, and the reaction was allowed to take place for 5 minutes. The reaction was terminated with 50 μl of 1N hydrochloric acid, and absorption at 490 nm was measured.

Effects of the Fas ligand on apoptosis-inducing activity was examined by $^{51}Cr$ release assay.

$10^6$ WC8 cells were incubated in RPMI1640 medium containing 20 μCi ($^{51}Cr$) sodium chromate (NEN) at 37° C. for 2 hours to label the cells with $^{51}Cr$. To the reaction solution containing $1 \times 10^4$ $^{51}Cr$-labeled cells were added the antiserum to a final concentration of 500 fold dilution, and subsequently, the culture supernatant of the extracellular domain of the Fas ligand derived from COS-1 cell (corresponding to the concentration of the extracellular domain of the Fas ligand of 0.9 μg/ml) to a final concentration of 10%. The reaction solution was incubated at 37° C. for 4 hours, and the apoptosis-inducing activity was measured by using the release of the $^{51}Cr$ for the index.

Table 1 shows the binding activity of the antiserum to the Fas ligand, and the effect of the antiserum on the apoptosis-inducing activity. In the western blotting, the antiserums prepared by the immunization with the M52 and the M57 peptides showed binding with the extracellular domain of the Fas ligand (+), while other antiserums failed to bind to the extracellular domain of the Fas ligand (−). In the plate assay, among the anti-peptide antiserums, the antiserums prepared by the immunization with the M52 and the M57 peptides exhibited a strong reaction (++) with the Fas ligand and the antiserums prepared by the immunization with the M53 and the M54 peptides also exhibited a fair reaction (+) with the Fas ligand. The apoptosis-supressing activity was found in none of the antiserums while the antiserum prepared by the immunization with the M52 showed the effect of enhacing the apoptosis-inducing activity of Fas ligand.

TABLE 1

Reactivity of the rabbit anti-peptide antiserum with the extracellular domain of the Fas ligand and effect of the antiserum on the apoptosis-inducing activity

| Antiserum | M52 | M53 | M54 | M55 | M56 | M57 | M59 |
|---|---|---|---|---|---|---|---|
| Results of Western blotting | + | − | − | − | − | + | − |
| Results of plate assay | ++ | + | + | − | − | ++ | − |
| Effects on apoptosis-inducing activity | promotion | − | − | − | − | − | − |

1-4 Purification of the antiserum

The antiserums (5 ml) prepared by the immunization with the M52 and the M57 peptides were purified by salting out and application through an ion exchange column.

To 5 ml of each antiserum was first added an equal volume of 0.15M NaCl, and then, saturated ammonium sulfate of an amount equal to the amount of the antiserum before its dilution with stirring. The stirring was continued at room temperature for another 30 minutes, and the mixture was allowed to stand for 30 minutes. The mixture was then centrifuged at 10,000 rpm for 10 minutes, and the resulting precipitate was dissolved in 5 ml of 0.02 M phosphate buffer, pH 6.3 and dialyzed. After removing the impurities by centrifugation, the solution was applied to a column packed with 10 ml of DEAE cellulose (DE52, WHATMAN) equilibrated with the same buffer. The fractions that were not adsorbed were collected, and the fractions collected by washing the column with an additional 50 ml buffer were mixed with the non-adsorption fractions. The thus obtained IgG-containing solution was concentrated by Diaflow PM10 membrane (AMICON) to obtain the purified antibody of each of the antiserums prepared by the immunization with the M52 and the M57 peptides. The protein concentrations of purified antibodies were calculated by absorption at 280 nm.

2. Preparation of anti-M52 peptide monoclonal antibody 2-1 Preparation of the antigen, and immunization of the mouse In 110 μl of 0.1M phosphate buffer, pH 7.0 was dissolved 1.1 mg of M52 peptide. In the meanwhile, 1.54 mg of maleimide-activated KLH (Boehringer-Mannheim) was dissolved in 154 μl of distilled water. The thus prepared solutions were mixed together, and the reaction was allowed to take place at room temperature for 2 hours. The reaction solution was then applied to Nick column (Pharmacia Biorech) that had been equilibrated with physiological saline to thereby purify and obtain the antigen for immunization.

70 μg of the thus prepared antigen for immunization was diluted to 0.1 ml with physiological saline, and mixed with an equal amount of the complete Freund's adjuvant (DIFCO). The solution was intraperitoneally administered to a female ddY mouse of five weeks old. After an interval of two weeks, the antigen of the same amount mixed with incomplete Freund's adjuvant (DIFCO) was administered in a similar manner.

2-2 Evaluation of the antiserum

One week after the administration, blood was collected from eyegrounds, and the antiserum was confirmed for binding with the extracellular domain of the Fas ligand.

First, 50 μl portions of the partially purified extracellular domain of the Fas ligand as will be described in 4-1 diluted to 0 to 25 ng/well with 0.076M PBS, pH 6.4 (hereinafter referred to as PBS) were dispensed in the wells of Immunoplate (Maxisorp, Nunc), and the Immunoplate was incubated at 45° C. for 30 minutes to immobilize the extracellular domain of the Fas ligand on the well. After washing the wells with ion exchange water for five times, 100 μl/well of 0.1% BSA/PBS was added to the wells for blocking of the well. After removing the blocking agent, the antiserum diluted with 0.1% BSA/PBS was added to the wells, and the reaction was done at 37° C. for 1 hour. The wells were then washed twice with 0.9% NaCl containing 0.005% Tween 20, and 50 μl/well of HRPO-labeled anti-mouse Igs antibody (DACO) diluted to 1,000 folds with 10% rabbit serum/PBS was added to the wells. The reaction was done at 37° C. for 1 hour. After the completion of the reaction, the wells were washed five times with the washing solution, and twice with ion exchange water, and 50 μl of 0.1M McIlvaine buffer (pH 5.0) containing 3 mg/ml o-phenylenediamine and 0.027% hydrogen peroxide was added to the wells, and the reaction was allowed to take place for 5 minutes. The reaction was terminated with 50 μl of 1N hydrochloric acid, and absorption at 490 nm was measured. The results indicate the strong reactivity between the mouse antiserum prepared by immunizing with the M52 peptide with the extracellular domain of the Fas ligand.

2-3 Preparation of the monoclonal antibody

A 70 μg portion of the antigen for immunization prepared in 2-1 was diluted with 400 μl physiological saline, and the solution was administered to a mouse with an increased antibody titer by injection to its tail vein. After three days, cell fusion was conducted in accordance with the procedure described in Ando, T. and Chiba, T., "Introduction to Experimental Operation Using Monoclonal Antibody", Kodansha-Scientific. After six days, the antibodies in the culture supernatant were screened by the procedure described in 2-2, and the wells exhibiting the positive reactivity were cloned by means of limiting dilution in accordance with the procedure described in Ando, T. and Chiba, T., "Introduction to Experimental Operation Using Monoclonal Antibody", Kodansha-Scientific. After the cloning, screening was conducted again to thereby obtain 20 clones (F918 series) of hybridomas producing the anti-M52 peptide monoclonal antibody that react with the Fas ligand. F918-4-5 (IgG1/λ), F918-2-4 (IgG1/λ), F918-7-3 (IgG1/κ), F918-9-4 (IgG1/λ), F918-17-1 (IgG1/κ), F918-20-2 (IgG1/λ), and F918-23-1 (IgG1/κ), as described below, were included in the F918 series. The subclasses of the hybridomas obtained included 3 clones of IgM/κ, 6 clones of IgG1/κ, 9 clones of IgG1/λ, 1 clone of IgG2b/λ, and 1 clone of IgG2b/κ. The hybridomas were cultivated in a serum-free medium (PHFM-II, GibcoBRL), and the culture supernatants were salted out with 60% saturated ammonium sulfate. IgG was applied to protein A column (PROSEP-A, BIOPROCESSING) for purification. The protein concentrations of thus obtained purified antibodies were calculated by measuring absorbance at 280 nm.

2-4 Evaluation of the antibody

Western blotting was carried out in accordance with the procedure described in 1-3 to confirm the binding of the two lots (F918-7-3 and F918-9-4) of the thus obtained purified antibodies (antibody concentration, 3 μg/ml) with the extracellular domain of the Fas ligand. The Fas ligand used were the purified extracellular domain of the Fas ligand as will be described in 4-1 (the extracellular domain of the Fas ligand derived from Pichia yeast shown in FIG. 2), the free Fas ligand derived from COS-1 cell as will be described in Example 5-1, and the extracellular domain of the Fas ligand derived from COS-1 cell as will be described in Example 3. HRPO-labeled anti-mouse Igs antibody (DACO) was used for the secondary antibody, and TMB reagent (SCYTEK Laboratories) was used for the detection. As shown in FIG. 2, with regard to F918-9-4, a band was detected at a molecular weight of about 30,000 for the extracellular domain of the Fas ligand derived from yeast, the extracellular domain of the Fas ligand derived from COS-1, and the free Fas ligand to confirm the binding of the antibody with the Fas ligand. With regard to F918-7-3, a band was detected for the extracellular domain of the Fas ligands derived from yeast and COS-1, while no band was detected for the free Fas ligand.

Figure 3:
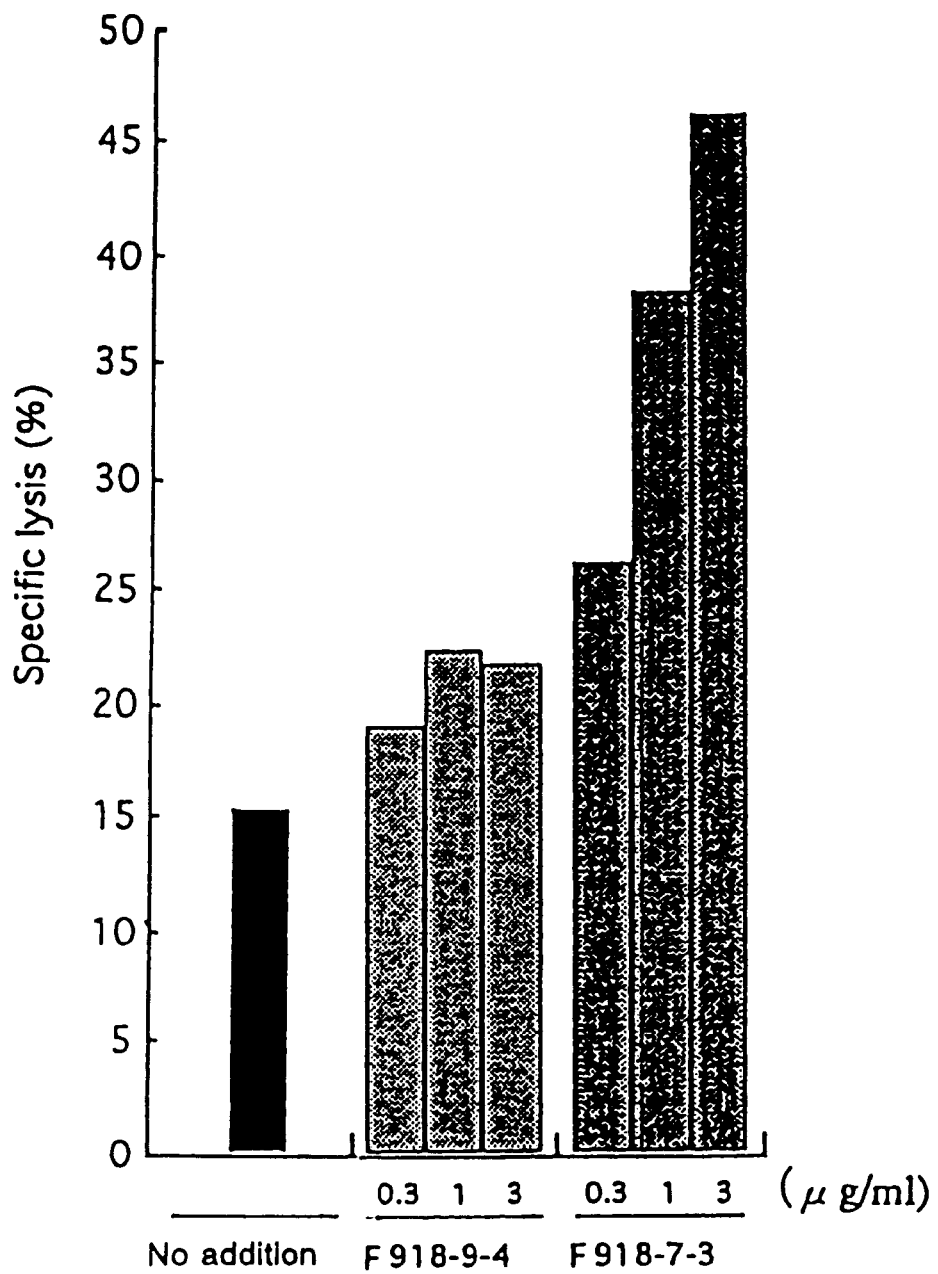
FIG. 3. A graph showing the effect of the anti-M52 peptide monoclonal antibody on the apoptosis-inducing activity.

Next, effect of the antibody on the apoptosis-inducing activity was examined in accordance with the procedure described in 1-3. As shown in FIG. 3, F918-9-4 did not significantly alter the apoptosis-inducing activity while F918-7-3 exhibited the activity of promoting the apoptosis induction. As demonstrated above, the monoclonal antibodies prepared by the immunization with the M52 peptide include at least two antibodies each having a specificity different from the other.

3. Preparation of anti-Fas ligand antibody 3-1 Preparation of the antigen, and immunization of the mouse The extracellular domain of the Fas ligand expressed from COS-1 cell prepared by the procedure as described below was used for the antigen for immunization.

The extracellular domain of the Fas ligand derived from COS-1 cell was prepared by employing a transformant COS-1/pM1070, which is the COS-1 cell having introduced therein a plasmid pM1070 described in Example 18 of International Patent Application Laid-Open No. WO95/13293. More illustratively, 8.1 μg of pM1070 was dissolved in 40 μl of 10 mM Tris-HCl (pH 7.4)/1 mM ethylenediamine tetraacetate (hereinafter abbreviated as TE buffer). To the solution was added 11.3 ml of D-MEM (Nippon Seiyaku K.K.) containing 1 ml of 0.2 mg/ml DEAE-dextran and 1 ml of 50 mM Tris-HCl, pH 7.4 to prepare DNA-DEAE-dextran mixed solution.

The DNA-DEAE-dextran mixed solution was added dropwise to the monolayer culture of COS-1 cells in a 150 cm$^2$ Roux flask grown to semiconfluency, and the culture was incubated at 37° C. in the presence of 5% $CO_2$ to obtain the transformant COS-1/pM1070. After 4 hours, DNA-DEAE dextran mixed solution was removed to replace the medium with D-MEM medium containing 10% fetal bovine serum (FBS, Irvine Scientific), and cultivation was continued for another 48 hours. The medium was then replaced with phenol red free D-MEM (with no FBS, BSA addition), and cultivation was continued for another 96 hours to recover the culture supernatant.

The culture supernatant was centrifuged at 1,200 rpm for 5 minutes to remove the precipitate, and then filtered through a filter of 0.22 μm. After concentrating to ten folds by Diaflow PM10 membrane (Amicon), 2.5 ml of the concentrate (corresponding to 22.5 μg) was subjected to gel filtration through PD10 column (Pharmacia) to collect a fraction of 3.5 ml eluted to voids. The thus collected fraction was concentrated to 400 μl by Centricon-10 (Amicon) to use the concentrate as the antigen for initial administration. In the meanwhile, 300 μl of the culture supernatant that had been concentrated to ten folds was subjected to 4–20% preparatory SDS-PAGE (2-D, TEFCO), and the gel near the molecular weight of 30,000 was cut out by referring to molecular weight marker (Prestained SDS-PAGE Standard Low, BIO-RAD Laboratories). The gel was finely divided and immersed overnight in physiological saline with shaking to extract the extracellular domain of the Fas ligand. The extract was concentrated to 200 μl by Centricon-10 (Amicon) to use the concentrate as the antigen for additional and final administrations.

A 200 μg portion of the thus prepared antigen for initial administration was mixed with an equal amount of the complete Freund's adjuvant (DIFCO), and the solution was intraperitoneally administered to a female ddY mouse of five week old. After an interval of two weeks, 100 μl of the antigen for the additional administration mixed with incomplete Freund's adjuvant (DIFCO) was administered in a similar manner.

3-2 Evaluation of the antiserum

Figure 4:
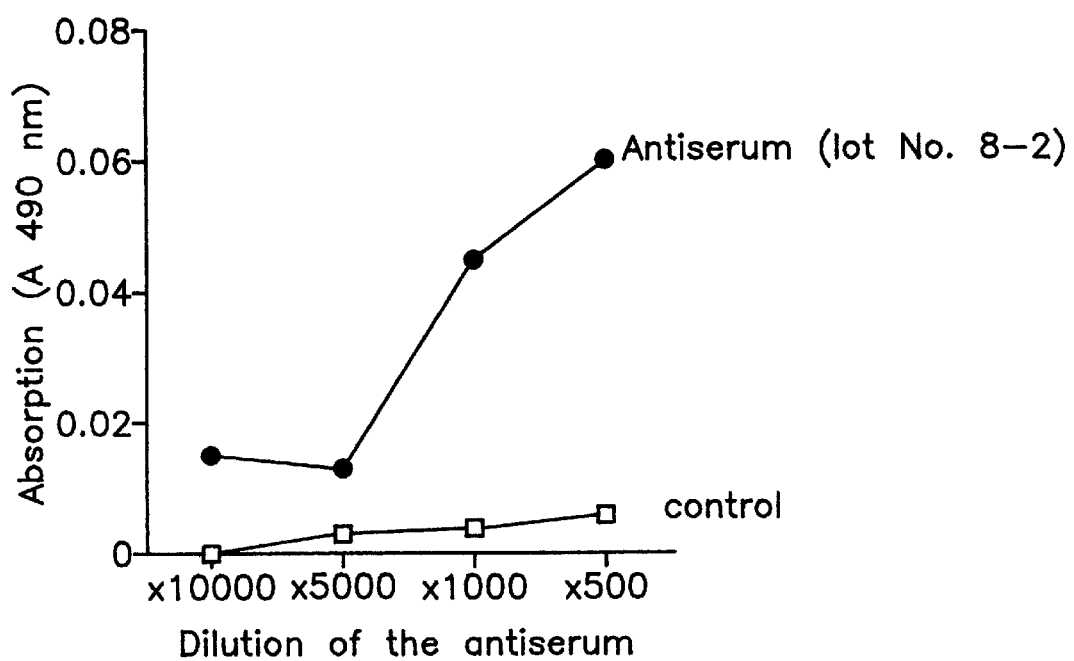
FIG. 4. A graph showing the antibody titer of the anti-Fas ligand antiserum (lot No. 8-2).

One week after the additional administration, blood was collected from eyegrounds, and the antiserum was evaluated for binding with the extracellular domain of the Fas ligand in accordance with the procedure described in 2-3. As shown in FIG. 4, the antiserum of the mouse (8-2) immunized with the partially purified extracellular domain of the Fas ligand derived from the COS-1 exhibited an increase in the absorption proportional to the degree of dilution, indicating the binding of the antiserum with the extracellular domain of the Fas ligand derived from the yeast. Effect of the antiserum on the apoptosis-inducing activity was also examined in accordance with the procedure described in 1-3, and it was then found that the antiserum has a strong inhibitory activity.

3-3 Preparation of monoclonal antibody

A 200 μl portion of the extracellular domain of the Fas ligand prepared by SDS-PAGE described in 3-1 was intraperitoneally administered to the mouse (8-2) whose serum had been confirmed for the binding activity with the extracellular domain of the Fas ligand derived from the yeast. After three days, cell fusion was conducted in accordance with the procedure described in Ando, T. and Chiba, T., "Introduction to Experimental Operation Using Monoclonal Antibody", Kodansha-Scientific. After six days, the antibodies in the culture supernatant were screened by two procedures, namely, by measuring the binding with the Fas ligand in accordance with the procedure described in 2-2, and by carrying out the screening with a sandwich EIA system for the purpose of obtaining the antibody that may be used for a sandwich assay with the anti-M 52 peptide antibody described in 1-4. First, 50 μl portions of DEAE-purified rabbit anti-M52 peptide antibody diluted to 10 μg/ml with PBS were dispensed in the wells of Immunoplate (Maxisorp, Nunc), and the Immunoplate was incubated at 45° C. for 30 minutes to immobilize the antibody on the well. After washing the wells with ion exchange water for five times, 100 μl/well of 0.1% BSA/PBS was added to the wells, and the wells were blocked at room temperature for 30 minutes. After removing the blocking agent, 25 μl of the partially purified extracellular domain of the Fas ligand as will be described in 4-1 at a concentration of 200 ng/ml, and then 25 μl of the culture supernatant were added to the wells, and the reaction was done at 37° C. for 1 hour. The wells were then washed twice with the washing solution, and 50 μl of HRPO-labeled anti-mouse Igs antibody (DACO) diluted to 1,000 folds with 10% rabbit serum/PBS was added to the wells. The reaction was done at 37° C. for 1 hour. After washing five times with the washing solution, and twice with ion exchange water, 50 μl of 0.1M McIlvaine buffer, pH 5.0 containing 3 mg/ml o-phenylenediamine and 0.027% hydrogen peroxide was added to the wells, and the reaction was allowed to take place for 10 minutes. The reaction was terminated with 50 μl of 1N hydrochloric acid, and absorption at 490 nm was measured.

In both screening procedures, one well of supernatant that reacts with the soluble Fas ligand described in 4-1 was obtained. The well exhibiting the reactivity was cloned by the limiting dilution in accordance with the procedure described in Ando, T. and Chiba, T., "Introduction to Experimental Operation Using Monoclonal Antibody", Kodansha-Scientific. After the cloning, screening was conducted by repeating the above-described procedure to obtain one clone of the hybridoma producing the antibody F919-9-18 (IgG2b/κ) that reacts with the extracellular domain of the Fas ligand and that may be used for a sandwich assay with the anti-M52 peptide antibody.

3-4 Evaluation of the Antibody

Figure 5:
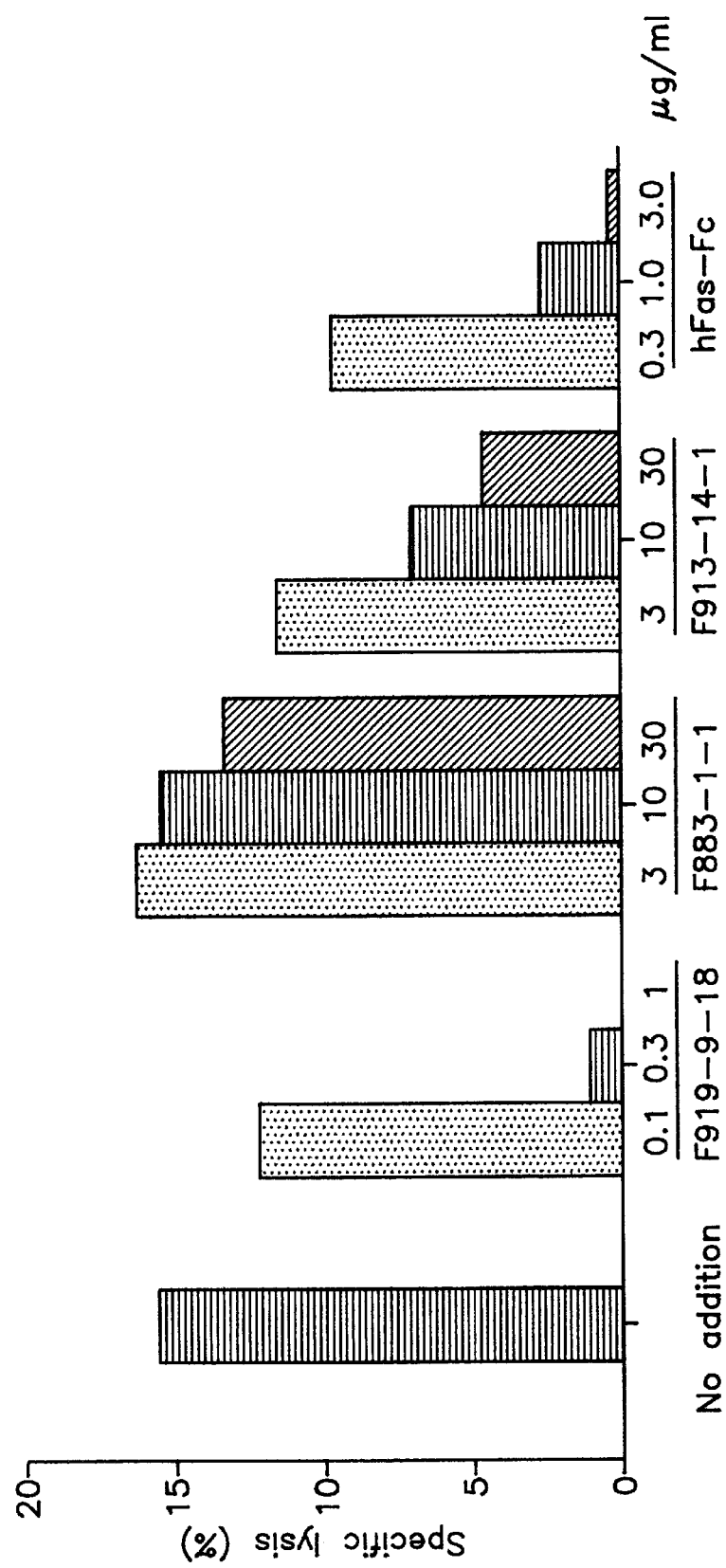
FIG. 5. A graph showing the apoptosis suppression activity of F919-9-18 monoclonal antibody.

The antibody F919-9-18 was evaluated for its apoptosis-suppression activity in accordance with the procedure described in 1-3. As demonstrated in FIG. 5, F919-9-18 showed a suppression activity stronger than the anti-Fas ligand antibody F883-1-1 described in Examples 15 and 16 of International Patent Application Laid-Open No. WO095-13293 by a factor or more than a hundred, and the suppression activity of the F919-9-18 was even stronger than the hFas-Fc described in Example 1 of the International Patent Application Laid-Open No. WO95-13293.

4. Preparation of the sandwich EIA system 4-1 Preparation of standard (1) Construction of plasmid pM1283 including the DNA coding the 179 amino acids in the extracellular domain of the human Fas ligand shown in SEQ ID No. 9 of the Sequence Listing First, sense primer 1 (TCTCTCGAGAAAAGAGAGCAGCTCTTCCACCTG) and antisense primer 1 (AGGGAATTCCTATTAGAGCTTATA) were chemically synthesized. The sense primer 1 includes the nucleotide sequence coding for a part of the α-factor signal sequence of Pichia yeast-expressing plasmid pPIC9 (Invitrogen), the nucleotide sequence coding for the N terminal region of the extracellular domain of the human Fas ligand, and XhoI site (CTCGAG). The antisense primer 1 includes the nucleotide sequence coding for the C terminal region of the extracellular domain of the human Fas ligand, termination codon (TAG), and EcoRI site (GAATCC).

A solution of 100 μl containing 100 pmol of each of the resulting primers; 50 ng of plasmid pM1070 including the DNA encoding the 179 amino acids of the extracellular domain of the human Fas ligand described in Example 18 of the International Patent Application Laid-Open No. WO95-13293; 20 nmol of each of DATP, dCTP, dGTP, and dTTP; and 2.5 units of Pfu DNA polymerase, and 10 μl of Pfu buffer attached with the Pfu DNA polymerase (Stratagene) was prepared. PCR cycles each comprising 94° C. (30 seconds), 55° C. (30 seconds), and 72° C. (1 minute) were repeated 30 times by using a DNA thermal cycler (PCR System 9600, Perkin Elmer). The resulting PCR product was double digested with EcoRI and XhoI, and incorporated in the EcoRI-XhoI site of pPIC9. The resulting plasmid was designated pM1283, and 20 μg of pM1283 was linearized by digestion with BglII for use in the transformation of the Pichia yeast.

(2) Transformation of Pichia yeast

Pichia yeast GS115 strain (Invitrogen) was inoculated in YPD plate (1% (w/v) bacto-yeast extract; 2% (w/v) peptone; 2% (w/v) D-glucose; 2% bacto-agar), and after cultivating at 30° C. for 2 days, a single colony was inoculated in YPD medium (1% (w/v) bacto-yeast extract; 2% (w/v) peptone; 2% (w/v) D-glucose). After an overnight cultivation with shaking at 30° C. and at 200 rpm, a yeast culture medium exhibiting an OD600 value in the range of from 0.2 to 0.3 was obtained.

The yeast culture medium was centrifuged at 1,500×g at room temperature for 5 minutes, and the thus separated yeast was suspended and washed in sterilized distilled water, and again subjected to centrifugation at 1,500×g for 5 minutes. By repeating such procedure, the yeast was further washed once with 20 ml SED buffer (0.95M sorbitol; 23.75 mM ethylenediamine tetraacetate (EDTA), pH 8.0; 50 mM DTT), and once with 20 ml 1M sorbitol, and then, resuspended in 20 ml SCE buffer (1M sorbitol; 1 mM EDTA; 10 mM sodium chloride buffer, pH 5.8). To 10 ml yeast suspension was added 7.5 μl of 3 mg/ml zymolyase (Invitrogen), and the suspension was incubated at 30° C. for 9 minutes to bring 70% of the yeast into the form of spheroplast by using the decrease of the OD600 value for the index. After the centrifugation at 750×g for 10 minutes, the yeast was washed once with 10 ml 1M sorbitol, and once with 10 ml CaS solution (1M sorbitol; 10 mM TrisHCl, pH 7.5; 10 mM CaCl$_2$), and suspended in 0.6 ml CaS solution.

To 0.1 ml of the spheroplast solution was added 10 μg linearized pM1283. After an incubation at room temperature for 10 minutes, 1 ml polyethylene glycol (PEG)/CaT solution (20% (w/v) PEG3350; 10 mM Tris, pH 7.5; 10 mM CaCl$_2$) was added to the solution, and the solution was further incubated at room temperature for 10 minutes. The solution was then centrifuged at 750×g for 10 minutes, and 150 μl SOS solution (1M sorbitol; 0.3×YPD; 10 mM CaCl$_2$) was added to the resulting pellet. After incubating the solution at room temperature for 20 minutes, 850 μl of 1M sorbitol was added to the solution.

A 100 μl portion of the thus obtained solution was added to 10 ml of histidine-free RD solution (0.186 g/ml sorbitol; 20 mg/ml D-glucose; 13.4 mg/ml yeast nitrogen base; 0.4 μg/ml biotin; 50 μg/ml L-glutamic acid; 50 μg/ml L-methionine; 50 μg/ml L-lysine; 50 μg/ml L-leucine; 50 μg/ml L-isoleucine; 1% agar) that had been maintained at 45° C. The resulting solution was layered on RDB plate (2% agar; RD solution), and incubated at 30° C. for 4 days. The resulting transformant was inoculated in MM plate (13.4 mg/ml yeast nitrogen base; 0.4 μg/ml biotin; 0.5% methanol, 1.5% agar) and MD plate (13.4 mg/ml yeast nitrogen base; 0.4 μg/ml biotin; 2% D-glucose, 1.5% agar), respectively, and incubation at 30° C. was continued for another 2 days. The transformant that propagated on the MD plate and that scarcely propagated on the MM plate was selected, and the thus selected transformant was used for the expression.

(3) Production of the extracellular domain of the human Fas ligand using the yeast The transformant prepared in (2) was incubated in 10 ml of BMGY (1% (w/v) yeast extract; 2% (w/v) peptone; 13.4 mg/ml yeast nitrogen base; 0.4 μg/ml biotin; 1% (v/v) glycerol; 0.1M potassium phosphate buffer, pH 6.0) in a 50 ml test tube with shaking at 30° C. for 2 days. The thus obtained culture medium was dispensed in 2 ml portions into 500 ml myer flasks each containing 100 ml BMGY, and 2 liters of culture medium with an OD 600 value of 10 to 20 was obtained by cultivation with shaking. The yeast was collected by centrifugation at 4,000×g at room temperature for 10 minutes, and suspended in 400 ml BMMY (1% (w/v) yeast extract; 2% (w/v) peptone; 13.4 mg/ml yeast nitrogen base; 0.4 μg/ml biotin; 0.5% (v/v) methanol; 0.1M potassium phosphate buffer, pH 6.0). The suspension was dispensed 50 ml portions into eight 500 ml myer flasks, and the incubation at 30° C. with shaking was continued for another 2 days. The resulting culture medium was centrifuged at 13,000×g for 10 minutes to obtain the culture supernatant containing the extracellular domain of the Fas ligand.

Figure 6:
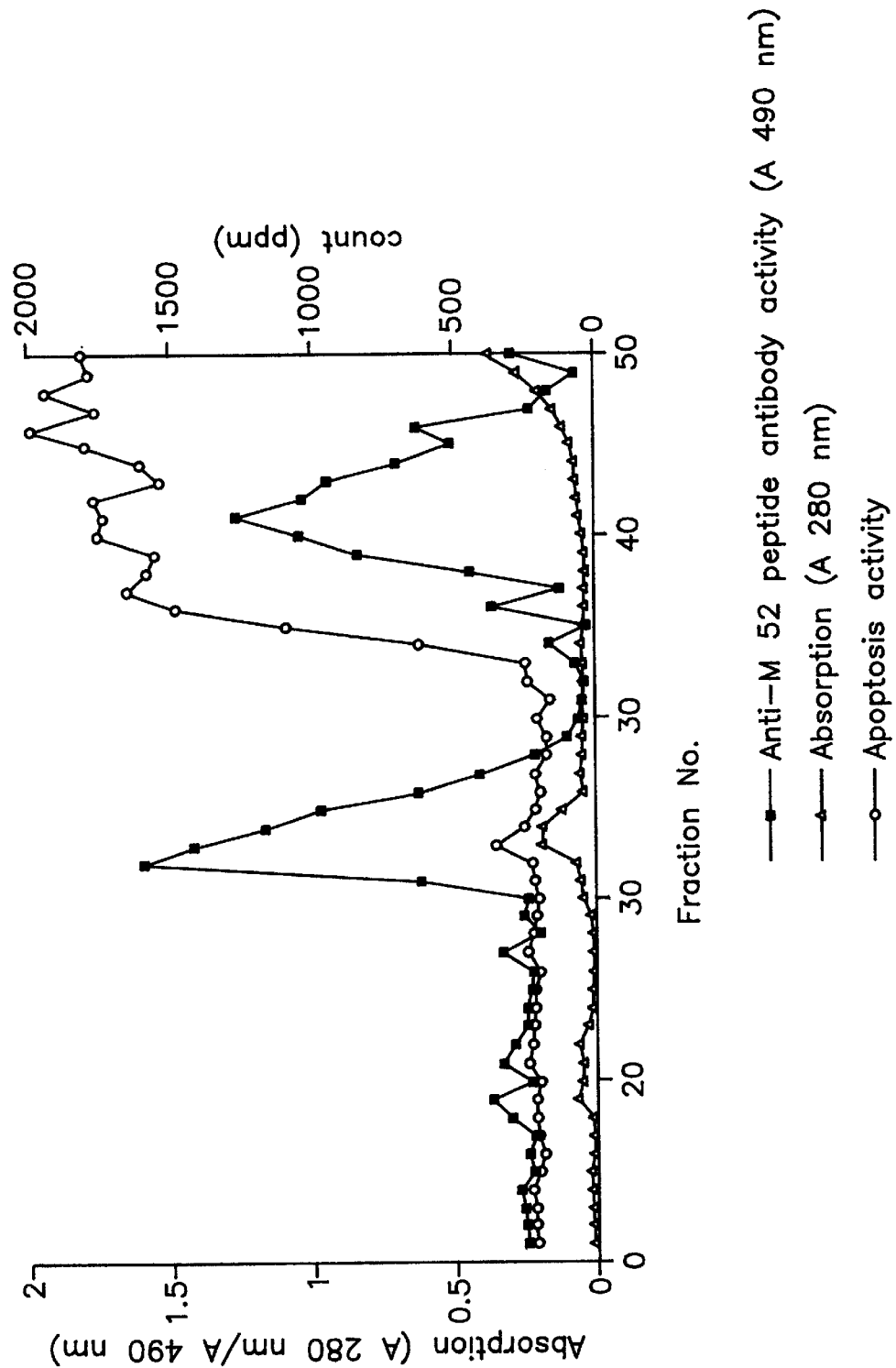
FIG. 6. A graph showing the results of gel filtration chromatography of the extracellular domain of the Fas ligand derived from yeast.

Next, 50 ml of the culture supernatant that had been filtered through a filter 0.22 μm was salted out with 80% saturated ammonium sulfate and allowed to stand at 4° C. for 1 hour. The precipitate was collected by centrifugation at 10,000 rpm for 10 minutes and dissolved in 0.067M phosphate buffer, pH 7.2 containing 0.15M NaCl, and the solution was subjected to dialysis. After the dialysis, impurities were further removed by centrifugation at 10,000 rpm for 10 minutes, and filtration through a filter of 0.22 μm. A 2 ml portion of the solution was applied to gel filtration column (Hiprep 16/60 Sephacryl S-300 HR, Pharmacia) for elution at a flow rate of 0.5 ml. The eluate was collected in 2 ml fractions, and the fractions were evaluated by absorption at 280 nm for protein detection. A 30 μl portion of each fraction was aliquoted for measurement of the apoptosis-inducing activity according to the procedure described in 1-3. A 50 μl portion of each fraction was also aliquoted for immobilization of the Immunoplate, and the Fas ligand was detected in accordance with the procedure described in 2-1 using the anti-M52 peptide antibody. FIG. 6 is the gel filtration chart, and the activity for binding with the anti-M52 peptide antibody was found in two series of fractions while the apoptosis-inducing activity was only found in the series of fractions with lower molecular weight. The fractions exhibiting the activity was examined by 4–20% SDS-PAGE (TEFCO), and it was then found that the band at a molecular weight of about 30,000 is only detected in the fractions with lower molecular weight exhibiting the apoptosis-inducing activity, and a band at a molecular weight of more than 140,000 is detected in the fractions with higher molecular weight. The fractions with higher molecular weight were then estimated to contain aggregated Fas ligand (hereinafter sometimes referred to as yeast Fas ligand aggregates). The fractions exhibiting the apoptosis-inducing activity were collected and concentrated with Centricon-10 (Amicon). The protein concentration of the concentrate was determined by Protein Assay (BioRad Laboratories) using BSA for the standard. The concentrate was used as a partially purified product of the extracellular domain of the human Fas ligand.

The purified extracellular domain of the Fas ligand was obtained by salting out the supernatant derived from the yeast with 80% saturated ammonium sulfate, dialyzing against 50 mM Tris-HCl, pH 8.0 containing 0.15M NaCl, and applying to an affinity column (5 ml) packed with protein A-Cellurofine (Chisso K.K.) having hFas-Fc bound thereto. The affinity column was prepared by binding the hFas-Fc described in Example 18 of International Patent Application Laid-Open No. WO95-13293 to the protein A-Cellurofine (Chisso K.K.) according to the instruction attached to the protein A-Cellurofine. After washing the column, the column was eluted with 50 mM Tris-HCl, pH 8.0 containing 2M NaCl, and the 280 nm peak fractions were collected. The thus collected fractions were dialyzed against 50 mM MES buffer, pH 6.0, and applied to MonoS (HR5/5, Pharmacia), which was eluted with 50 mM MES buffer, pH 6.0 containing 500 mM NaCl to collect 280 nm peak fractions. The fractions collected were concentrated by Centricon-10 (Amicon), and the concentrate was dialyzed against PBS. Protein concentration was measured by Lowry method by using BSA for the standard. The purified extracellular domain of the human Fas ligand in an amount of 38 μg (protein concentration, 300 μg/ml) was obtained.

4-2 Preparation of sandwich EIA system using polyclonal antibody

Figure 7:
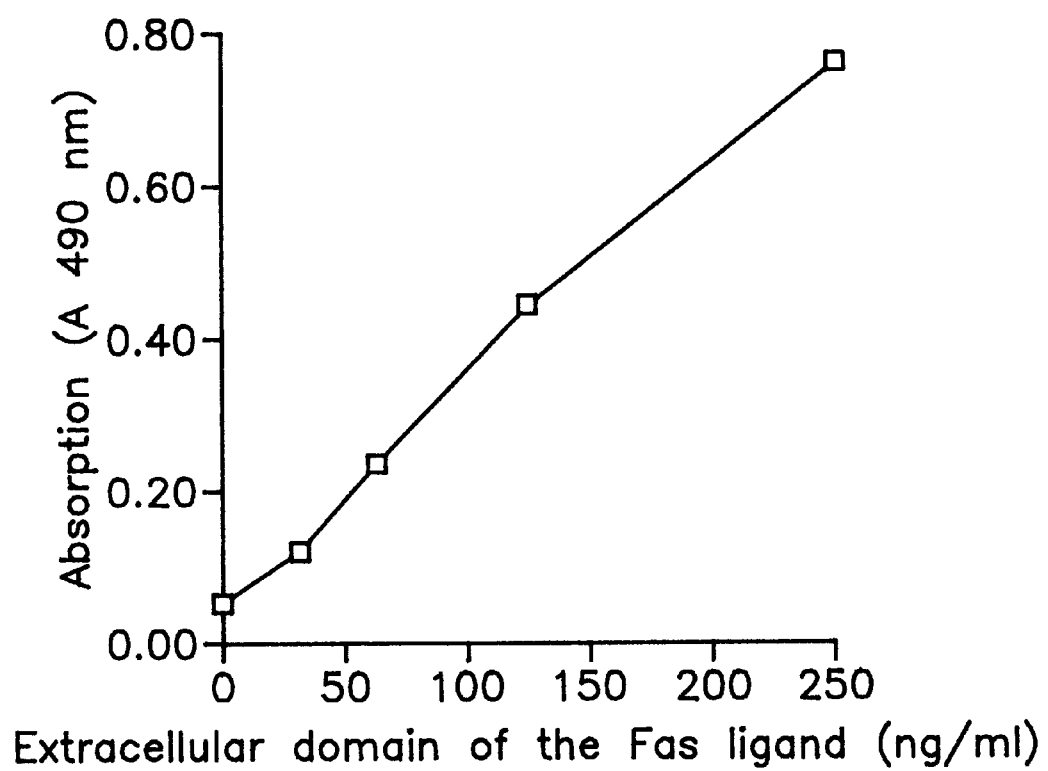
FIG. 7. A graph showing the standard curve of the sandwich EIA system using a polyclonal antibody.

A sandwich EIA system was prepared by using DEAE-purified rabbit anti-M52 peptide antibody and anti-Fas ligand antiserum (lot 8-2). First, 50 μl/well of DEAE-purified rabbit anti-M52 peptide antibody diluted to 10 μg/ml with PBS was dispensed in the wells of Immunoplate (Maxisorp, Nunc), and the Immunoplate was incubated at 45° C. for 30 minutes to immobilize the antibody on the well. After washing the wells with ion exchange water for five times, 100 μl/well of 0.1% BSA/PBS was added to the wells, and the wells were blocked at room temperature for 30 minutes. After removing the blocking agent, 25 μl of the purified extracellular domain of the Fas ligand diluted with 0.1% BSA/PBS to a concentration of 1 to 250 ng/ml, and then 25 μl of the anti-Fas ligand antiserum (lot 8-2) diluted with 0.1% BSA/PBS to 500 folds were added to the wells, and the reaction was done at 37° C. for 1 hour. The wells were then washed twice with 0.9% NaCl containing 0.005% Tween 20, and 50 μl of HRPO-labeled anti-mouse Igs antibody (DACO) diluted to 1,000 folds with 10% rabbit serum/PBS was added to the wells. The reaction was done at 37° C. for 1 hour. After washing five times with the washing solution, and twice with ion exchange water, 50 μl of 3 mg/ml o-phenylenediamine/0.1M McIlvaine buffer, pH 5.0 containing 0.027% hydrogen peroxide was added to the wells, and the reaction was allowed to take place for 10 minutes. The reaction was terminated with 50 μl of 1N hydrochloric acid, and absorption at 490 nm was measured with spectrophotometer. FIG. 7 shows the standard curve. The sandwich EIA system prepared was concluded to be capable of quantitatively measuring the Fas ligand at a high sensitivity.

4-3 Preparation of sandwich EIA system using monoclonal antibody

A sandwich EIA system using the monoclonal antibody was prepared as described below.

First, the monoclonal antibody was labeled with peroxidase in accordance with the procedure described in Nakane et al., "Immunofluorescence and Related Staining Techniques", Knapp, W., Holubar, K. and Wick, G. eds., 1978. More illustratively, 6 mg of peroxidase (RZ3.11, Toyobo Co., Ltd.) was weighed and dissolved in 1.5 ml of distilled water, and 0.3 ml of 0.1M sodium metaiodate in distilled water was added to this solution. After allowing the solution to stand at room temperature for 15 minutes, 0.3 ml of 1.5% ethylene glycol in distilled water was added, and the solution was allowed to stand at room temperature for 20 minutes. The resulting solution was dialyzed overnight against 0.001M acetate buffer, pH 4.4.

To 127 μl of the resulting activated peroxidase (corresponding to 400 μg of peroxidase) was added 7 μl of the 1M carbonate buffer, pH 9.5, and then, 500 μg of the purified monoclonal antibody (2 to 3 mg/ml) dialyzed against 0.01M carbonate buffer, pH 9.5, and the solution was incubated at 25° C. for 2 hours for reaction. To the solution was then added 12 μl of 4 mg/ml sodium borohydrate in 0.01M carbonate buffer, pH 9.5, and the solution was allowed to stand at 4° C. for 2 hours. The solution was then dialyzed overnight at 4° C. against 0.076M PBS, pH 6.4, and the resulting peroxidase-labeled antibody was stored at 20° C. after adding half its volume of 18% sucrose and 0.3% BSA/PBS.

Next, 50 μl/well of the monoclonal antibodies of F918 series and F919-18 were respectively dispensed in the wells of Immunoplate (Maxisorp, Nunc), and the Immunoplate was incubated at 45° C. for 30 minutes to immobilize the antibody on the well. After washing the wells with ion exchange water for five times, 0.1% BSA/PBS was added to the wells for blocking of the well and the well was incubated at room temperature for 30 minutes. After removing the blocking agent, 25 μl of the purified extracellular domain of the Fas ligand diluted with 0.1% BSA/PBS to a concentration of 0 to 100 ng/ml, and then 25 μl of the HRPO-labeled antibody (F918 series or F919-9-18) diluted with 10% rabbit serum/PBS to 0.5 to 2 μg/ml were added to the wells, and the reaction was promoted at 37° C. for 1 hour. The wells were then washed five times with 0.9% NaCl washing solution containing 0.005% Tween 20, and twice with ion exchange water. To the well was then added 50 μl of 3 mg/ml o-phenylenediamine/0.1M McIlvaine buffer, pH 5.0 containing 0.027% hydrogen peroxide, and the reaction was allowed to take place for 10 minutes. The reaction was terminated with 50 μl of iN hydrochloric acid, and absorption at 490 nm was measured with spectrophotometer. Table 2 shows the combinations of the monoclonal antibodies and the results obtained by employing such antibody combinations in the EIA. The results demonstrate the possibility of combining the anti-M52 peptide monoclonal antibody (F918 series) with the anti-Fas ligand antibody (F919). Sandwich systems employing the combination of F918-9-4/F918-7-3 comprising two anti-M52 peptide monoclonal antibodies, and the combination of F919-9-18/F919-9-18 comprising the same antibody were also possible. It should be noted that in Table 2, "Hgih" indicates high reactivity; "Fair" indicates fair reactivity; "Low" indicates low reactivity; and "No" indicates no reactivity. In Table 2, rabbit anti-M52 and rabbit anti-M57 are antiserums of the rabbits immunized with M52 and M57 peptide, respectively.

TABLE 2

Various combinations of anti-Fas ligand antibodies in sandwich EIA system

| B | A | | | | | | | | | |
|---|---|---|---|---|---|---|---|---|---|---|
|   | Rabbit anti-M52 | Rabbit anti-M57 | F918-9-4 | F918-7-3 | F918-23-1 | F918-4-5 | F918-17-1 | F918-2-4 | F918-20-2 | F919-9-18 |
| Rabbit anti-M52 | No | No | No | No | No | Low | Low | Low | No | High |
| Rabbit anti-MS7 | No | No | No | No | No | No | Low | No | No | Fair |
| F918-9-4 | No | No | No | Low | No | No | No | No | No | High |
| F918-7-3 | NO | NO | Fair | No | NO | Low | Fair | Fair | Low | High |
| F918-23-1 | No | No | No | No | No | No | No | No | No | Low |
| F918-4-5 | No | No | No | Fair | No | No | No | No | No | High |
| F918-17-1 | No | No | No | Low | No | No | No | No | No | High |
| F918-2-4 | NO | NO | NO | Fair | NO | NO | NO | NO | NO | High |
| F918-20-2 | Low | No | No | Fair | No | No | No | No | No | High |
| F919-9-18 | Fair | NO | High | High | Low | Fair | Fair | Fair | Low | High |

A: Labeled antibody
B: Solid phase-immobilized antibody

5. Evaluation of assay system 5-1 Preparation of various Fas ligands

Polypeptides nd42 and cd179, which are the deletion mutants of the extracellular domain of the human Fas ligand were expressed by the procedure described in Example 21 of the International Patent Application Laid-Open No. WO95-13293. It should be noted that in the specification of the International Patent Application, the polypeptides nd42 and cd179 are respectively designated ND42 and CD179.

Polypeptides nd5, nd12, nd20, nd32 and nd49, which are the deletion mutants of the extracellular domain of the human Fas ligand; the polypeptide L179F, which is the substitution mutants of the extracellular domain of the human Fas ligand; and free Fas ligand were expressed by the procedure as will be described below.

It should be noted that the polypeptides nd5, nd12, nd20, nd32, nd42, and nd 49 are the polypeptides wherein 5 amino acids, 12 amino acids, 20 amino acids, 32 amino acids, 42 amino acids, and 49 amino acids have been respectively deleted from the N terminal of the amino acid sequence described in SEQ ID No. 9 in the Sequence Listing; namely, the polypeptides having the amino acid sequences respectively extending from 6th, 13th, 21st, 33rd, 43rd and 50th amino acid to 179th amino acid. The polypeptide cd179 is the polypeptide wherein 1 amino acid has been deleted from the C terminal of the amino acid sequence described in SEQ ID No. 9 in the Sequence Listing; namely, the polypeptide having the amino acid sequence of amino acid Nos. 1 to 178. The polypeptide L179F is the polypeptide wherein leucine, which is the C terminal amino acid residue in the amino acid sequence described in SEQ ID No. 9 in the Sequence Listing, has been substituted with phenylalanine. The free Fas ligand is the Fas ligand expressed on the surface of the COS-1 cell released into the culture supernatant, and the COS-1 cell used of the expression is the cell into which a plasmid including the full length Fas ligand has been introduced.

(1) Preparation of the plasmid pM1081

The plasmid pM1081 coding for the signal peptide of the human Fas antigen and the extracellular domain of the human Fas ligand was prepared by the procedure as described below. As a consequence of silent mutation, the pM1081 has SpeI and PshAI recognition sites introduced in the sequence coding for the signal peptide of the human Fas antigen, and PstI recognition site introduced in the sequence coding for the human Fas ligand.

First, sense primer 2 (TGCGAATTCACCATGCTGGGCATCTGG) and antisense primer 2 (CTTCTGCAGGTGGAAGAGCTGAGCGACACTAGTCAGAACCAGAGG) were chemically synthesized. The sense primer 2 includes the 5' terminal region of the sequence coding for the signal peptide of the human Fas antigen; and EcoRI site (GAATTC). The antisense primer 2 includes a sequence coding for the N terminal side of the extracellular domain of the human Fas ligand and the C terminal side of the sequence coding for the signal peptide of the human Fas antigen; PstI site (CTGCAG); SpeI site (ACTAGT); and PshAI site (GACTAGTGTC). A 100 µl solution containing 100 pmol of each of the resulting antisense primer 2 and the sense primer 2; 50 ng of plasmid pBLF including the DNA coding for the human Fas antigen (Itoh, N. et al., Cell, vol. 66, 233–243, 1991); and 2.5 U of Pfu DNA polymerase and 10 µl of Pfu buffer included in the Pfu DNA polymerase set (Stratagene) was prepared. PCR cycles each comprising 94° C. (30 seconds), 55° C. (30 seconds), and 72° C. (1 minute) were repeated 30 times by using a DNA thermal cycler (PCR System 9600, Perkin Elmer). The PCR product was double digested with EcoRI and PstI, and the digestion product was electrophoresed on agarose gel. The DNA fragment of about 70 bp was collected and the DNA was purified by QIAEX kit (QIAGEN). The DNA of about 70 bp as described above was inserted in the EcoRI-PstI site of plasmid pM1067 described in Example 1 of the International Patent Application Laid-Open No. WO95-13293.

When the nucleotide sequence of the resulting plasmid was confirmed, a 16 bp deletion was found between the EcoRI site and the SpeI site. In order to construct the sequence between the EcoRI site and the SpeI site, sense oligonucleotide 1 (AATTCACCATGCTGGGCATCTGGACCCTCCTACCTCTGGTTCTGA) and antisense oligonucleotide 1 (CTAGTCAGAACCAGAGGTAGGAGGGTCCAGATGCCCAGCATGGTG) were chemically synthesized, and a 20 µl TE solution containing 1 nmol of each of the sense oligonucleotide 1 and the antisense oligonucleotide 1 were prepared. The TE solution was heated to 95° C. for 5 minutes, and gradually cooled to 16° C. to thereby anneal the nucleotides and produce a DNA fragment having the EcoRI cleavage site and the SpeI cleavage site on opposite ends. The thus produced DNA fragment was inserted between the EcoRI site and the SpeI site of the above-described plasmid with 16 bp deletion to thereby obtain pM1081.

(2) Preparation of plasmid pM1291

First, sense primer 3 (CTGACTAGTGTCGCTCAGAAGGAGCTGGCA) and antisense primer 3 (GTCTTCCCATTCCAGAGGCATGG) were chemically synthesized. The sense primer 3 includes the nucleotide sequence coding for the amino acid sequence located on C terminal side of the signal peptide of the human Fas antigen and the amino acid sequence of 6th to 10th amino acids from N terminal of the extracellular domain of the human Fas ligand; SpeI site (ACTAGT); and PshAI site (GACTAGTGTC). The antisense primer 3 is the sequence complementary to the nucleotide sequence of the 164th to 186th nucleotides in the cDNA of the extracellular domain of the human Fas ligand, and includes BstXI site (CCAGAGGCATGG). A 100 µl solution containing 100 pmol of each of the thus prepared sense primer 3 and antisense primer 3; 50 ng of pBX-hFL1 described in Example 1 of the International Patent Application Laid-Open No. WO95-13293; 20 nmol of each of DATP, dCTP, dGTP, and dTTP; and 2.5 units of Pfu DNA polymerase, and 10 µl of Pfu buffer was prepared. PCR was carried out by repeating the procedure of the above (1). The resulting PCR product was double digested with SpeI and BstXI, and incorporated in the SpeI-BstXI site of the plasmid pM1081 prepared in (1). The resulting plasmid was designated pM1291.

(3) Preparation of plasmid pM1292

First, sense primer 4 (CTGACTAGTGTCGCTCGAGAGTCTACCAGC) was chemically synthesized. The sense primer 4 includes the nucleotide sequence coding for the amino acid sequence located on C terminal side of the signal peptide of the human Fas antigen and the amino acid sequence of 13th to 17th amino acids from N terminal of the extracellular domain of the human Fas ligand; SpeI site (ACTAGT); and PshAI site (GACTAGTGTC).

PCR was carried out by repeating the procedure of (2) using the sense primer 4 and the antisense primer 3 of (2). The resulting PCR product was double digested with SpeI and BstXI, and incorporated in the SpeI-BstXI site of pM1081 prepared in (1). The resulting plasmid was designated pM1292.

(4) Preparation of plasmid pM1293

First, sense primer 5 (CTGACTAGTGTCGCTACAGCATCATCTTTG) was chemically synthesized. The sense primer 5 includes the nucleotide sequence coding for the amino acid sequence located on C terminal side of the signal peptide of the human Fas antigen and the amino acid sequence of 21st to 25th amino acids from N terminal of the extracellular domain of the human Fas ligand; SpeI site (ACTAGT); and PshAI site (GACTAGTGTC).

PCR was carried out by repeating the procedure of (2) using the sense primer 5 and the antisense primer 3 of (2). The resulting PCR product was double digested with SpeI and BstXI, and incorporated in the SpeI-BstXI site of pM1081. The resulting plasmid was designated pM1293.

(5) Preparation of plasmid pM1295

First, sense primer 6 (CTGACTAGTGTCGCTAGTCCACCCCCTGAA) was chemically synthesized. The sense primer 6 includes the nucleotide sequence coding for the amino acid sequence located on C terminal side of the signal peptide of the human Fas antigen and the amino acid sequence of 33rd to 37th amino acids from N terminal of the extracellular domain of the human Fas ligand; SpeI site (ACTAGT); and PshAI site (GACTAGTGTC).

PCR was carried out by repeating the procedure of (2) using the sense primer 6 and the antisense primer 3 of (2). The resulting PCR product was double digested with SpeI and BstXI, and incorporated in the SpeI-BstXI site of pM1081. The resulting plasmid was designated pM1295.

(6) Preparation of plasmids pM1296, pM1297, pM1298, and pM1300

The plasmids pM1291, pM1292, pM1293, and pM1295 prepared in (2) to (5) were double digested with EcoRI and KpnI, respectively, and the digestion products were subjected to agarose gel electrophoresis. The DNA fragments of about 580, 570, 540, and 500 bp were respectively collected, and the DNAs were purified by QIAEX kit (QIAGEN). The above-described DNA fragments of about 580, 570, 540, and 500 bp were respectively incorporated in the EcoRI-KpnI site of pM1103 prepared by recombination modifying the animal cell expression vector pEF-BOS (Mizushima and Nagata, Nucleic Acids Res., vol. 18, 5322, 1990) with dhfr gene. The resulting plasmids were designated pM1296, pM1297, pM1298, and pM1300, respectively.

The nucleotide sequence of the thus prepared plasmids was determined by using PRISM Dye Terminater Cycle Sequencing kit (Perkin-Elmer) and DNA sequencer (Model 373A, Perkin-Elmer). It was then found that the plasmids pM1296, pM1297, pM1298, and pM1300 respectively included the DNAs described in SEQ ID Nos. 1, 2, 3 and 4 in the Sequence Listing of International Patent Application No. PCT/JP95/00883, which are respectively the nucleotide sequences coding for the amino acid sequences after 6th, 13th, 21st and 33rd amino acid from the N terminal of the extracellular domain of the Fas ligand. The inventors of the present invention transformed E. coli HB101 with plasmids pM1297 and pM1300, respectively, by a known procedure, and the resulting transformant E. coli HB101 (pM1297) and HB101 (pM1300) were deposited to National Institute of Bioscience and Human-Technology Agency of Industrial Science and Technology on Apr. 26, 1995 (Accession Nos. FERM BP-5083, FERM BP-5084).

(7) Preparation of plasmid pM1070-pUC118 including the DNA coding for the extracellular domain of the human Fas ligand First, sense primer 2 (TGCGAATTCACCATGCTGGGCATCTGG) and antisense primer 4 (AACCTGCAGGTGGAAGAGCTGAGCAACAGACGTAAG) were chemically synthesized. The sense primer 2 includes EcoRI site (GAATTC), and the nucleotide sequence coding for the 5 amino acids on the N terminal of the signal peptide of the human Fas antigen. The antisense primer 4 includes PstI site (CTGCAG); the nucleotide sequence coding for the 4 amino acids on the N terminal of the extracellular domain of the human Fas ligand; and the nucleotide sequence coding for the 5 amino acids on the C terminal of the signal peptide of the human Fas antigen.

A 100 µl solution containing 100 pmol of each of the resulting primers; 50 ng of plasmid pBLF 58-1 including the DNA coding for the amino acids of the human Fas antigen (Itoh, N. et al., Cell, vol. 66, 233–243, 1991); 20 nmol of each of DATP, dCTP, dGTP, and dTTP; and 2.5 U of Pfu DNA polymerase and 10 µl of Pfu buffer was prepared. PCR cycles each comprising 94° C. (30 seconds), 55° C. (30 seconds), and 72° C. (1 minute) were repeated 30 times by using a DNA thermal cycler (PCR System 9600, Perkin Elmer). The PCR product was double digested with EcoRI and PstI, and the digestion product was electrophoresed on agarose gel. The DNA fragment of about 70 bp was collected and the DNA was purified by QIAEX kit (QIAGEN). The plasmid pM1067 described in Example 1 of the International Patent Application Laid-Open No. WO95-13293 was double digested with EcoRI and PstI, and the above-described DNA fragment of about 70 bp was inserted in the thus digested plasmid to obtain plasmid pM1070-pUC118.

(8) Preparation of plasmid pM1090 including the DNA coding for L179F, which is a mutant extracellular domain of the Fas ligand with C terminal amino acid substitution First, sense primer 7 (GAGCTACTGCACTACTGGGC) and antisense primer 5 (CTTGGTACCCTATTAGAACTTATATAAGCC) were chemically synthesized. The sense primer 7 includes 20 bp DNA coding for the 129th to 135th amino acids in the extracellular domain of the human Fas ligand; and ApaI site (GGGCCC) is located 6 bp in the downstream. The antisense primer 5 includes the nucleotide sequence coding for the 175th to 178th amino acids from the C terminal of the extracellular domain of the human Fas ligand, and the nucleotide sequence coding for 179th leucine (CTC) is substituted with the nucleotide sequence coding for phenylalanine (TTC). The antisense primer 5 also includes termination codon (TAA, TAG) and KpnI site (GGTACC).

PCR was carried out by repeating the procedure of (2) using the sense primer 7 and the antisense primer 5. The resulting PCR product was double digested with ApaI and KpnI, and the digestion product was electrophoresed on agarose gel. The DNA fragment of about 130 bp was collected and the DNA was purified by QIAEX kit (QIAGEN). The plasmid pM1070-pUC118 including the DNA coding for the extracellular domain of the human Fas ligand was double digested with ApaI and KpnI, and the above-described DNA fragment of about 130 bp was inserted in the linearized plasmid. The resulting plasmid was double digested with EcoRI and KpnI, and the digestion product was electrophoresed on agarose gel. The DNA fragment of about 600 bp was collected and purified by QIAEX kit. The above-described DNA fragments of about 600 bp was incorporated in the cloning EcoRI-KpnI site of the pM1103 prepared by incorporating the dFHR gene in the animal cell expression vector pEF-BOS (Mizushima and Nagata, Nucleic Acids Res., vol. 18, 5322, 1990). The resulting plasmid was designated pM1090.

The nucleotide sequence of the thus prepared plasmid was determined by using PRISM Dye Terminater Cycle Sequencing kit (Perkin-Elmer) and DNA sequencer (Model 373A, Perkin-Elmer). It was then confirmed that the plasmid pM1090 included the DNA coding for the amino acid sequence which is the amino acid sequence of the extracellular domain of the human Fas ligand (SEQ ID No. 9 in the Sequence Listing) wherein its C terminal amino acid residue, leucine has been substituted with phenylalanine.

(9) Transformation into COS-1 cell pM1090, pM1296, pM1297, pM1298, pM1300, pM1070 described in Example 18 of the International Patent Application Laid-Open No. WO95-13293, and pEX-hFL1 described in Example 12 of the International Patent Application Laid-Open No. WO95-13293 were used for the procedure as described below to prepare transformants COS-1/pM1090, COS-1/pM1296, COS-1/pM1297, COS-1/pM1298, COS-1/pM1300, COS-1/pM1070, and COS-1/pEX-hFL1.

More illustratively, 8.1 µg of each of the plasmid DNA was dissolved in 40 µl Tris/EDTA solution. To 2.5 µl portion of the solution was added 0.7 ml of D-MEM (Nissui Seiyaku) containing 0.2 g/ml DEAE-dextran and 50 mM Tris-HCl, pH 7.4 to prepare DNA-DEAE-dextran mixed solution. The DNA-DEAE-dextran mixed solution was added to the monolayer culture of COS-1 on 6 well plate grown to semiconfluency, and the plate was incubated at 37° C. in the presence of 5% $CO_2$ to obtain the transformants COS-1/pM1090, COS-1/pM1296, COS-1/pM1297, COS-1/pM1298, COS-1/pM1300, COS-1/pM1070, and COS-1/pEX-hFL1.

Each of the thus obtained transformants COS-1/pM1090, COS-1/pM1296, COS-1/pM1297, COS-1/pM1298, COS-1/pM1300, COS-1/pM1070 of and COS-1/pEX-hFL1 was cultivated in D-MEM containing 1% FBS at 37° C. for 72 hours, and the culture supernatant was collected. The culture supernatants were evaluated for their apoptosis-inducing activity by the procedure described in Examples 1 to 3.

(10) Free Fas ligand

Free Fas ligand used was the one recovered from the supernatant of the transformant COS-1/pEX-hFL1 prepared by introducing the plasmid pEX-hFL1 described in Example 12 of the International Patent Application Laid-Open No. WO95-13293 into the COS-1 cell in accordance with the procedure described in the above (9) (free Fas ligand is hereinafter sometimes referred to as COS free).

It is reported that a specific matrix metaloproteinase-like enzyme cleaves membrane-bound Fas ligand to produce its soluble (free) form (Tanaka M. et al., EMBO J. 14: 1129–1135 (1995), Tanaka M. et al., Nature Medicine 2: 317–322 (1996)).

be noted that "High" indicates high reactivity; "Low" indicates low reactivity; and "No" indicates no reactivity.

TABLE 3

Various Fas ligands with which the sandwich EIA system reacts

|  | Yeast FasL | Yeast FasL aggregate | COS sFasL | COS free | nd5 | nd12 | nd20 | nd32 | nd42 | nd49 | cd179 | L179F |
|---|---|---|---|---|---|---|---|---|---|---|---|---|
| Apoptosis activity | YES | NO | YES | YES | YES | YES | YES | YES | YES | NO | NO | YES |
| M52 F919 serum | High | No | High | No | High | High | High | No | No | No | No | High |
| F918-7-3 F918-9-4-HHP | High | No | High | No | High | High | High | No | No | No | High | High |
| M52 F919-9-18-HRP | High | No | High | Low | High | High | High | No | No | No | No | Low |
| F919-9-18 F918-7-3-HRP | High | No | High | No | High | High | High | No | No | No | No | Low |
| F918-7-3 F919-9-18-HRP | High | No | High | Low | High | High | High | No | No | No | No | High |
| F918-9-4 F919-9-18-HRP | High | No | High | High | High | High | High | High | No | No | No | High |
| F918-4-5 F919-9-18-HRP | High | No | High | High | High | High | High | High | No | No | No | High |
| F919-9-18 F919-9-18-HRP | High | No | High | High | High | High | High | High | High | No | No | High |

5-2 Reactivity with various Fas ligand

Sandwich EIA system of 8 types were employed to evaluate antigen specificity of various Fas ligands. Various deletion and substitution mutants of the extracellular domain of the Fas ligand; the aggregated extracellular domain of the Fas ligand (yeast FasL aggregate) and the purified extracellular domain of the Fas ligand (yeast FasL) described in 4-1; the extracellular domain of the Fas ligand derived from COS-1 cell (COS sFasL) described in 3-1; and free Fas ligand (COS free) were used for the Fas ligands to determine the reactivity with each of such Fas ligands.

Figure 8:
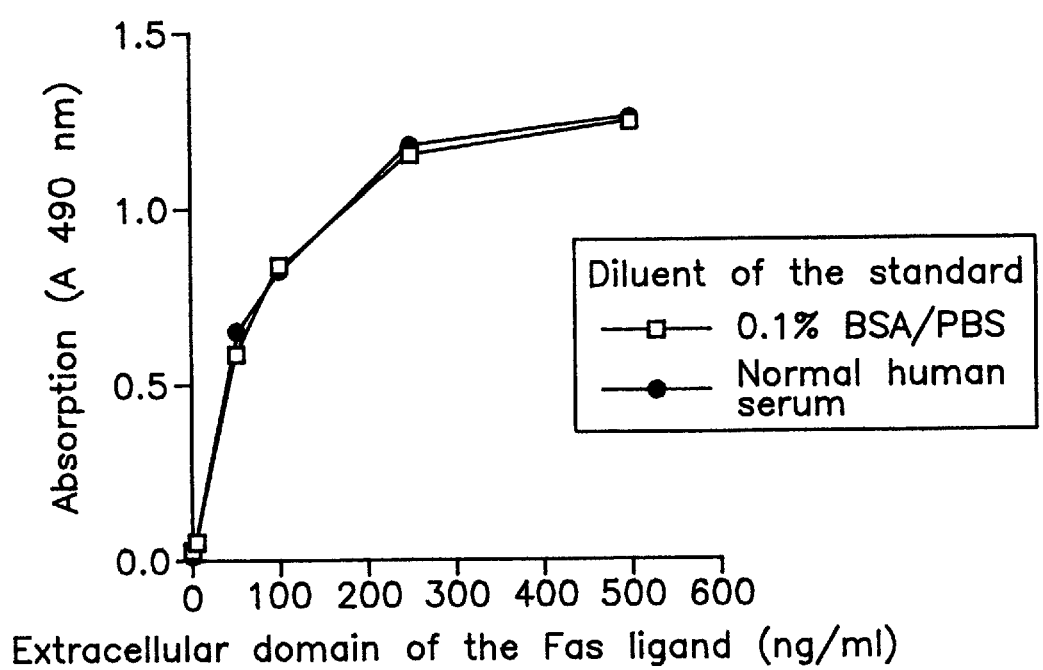
FIG. 8. A graph showing the effect of normal human serum in the sandwich EIA system.

As demonstrated in Table 3, the monoclonal antibodies obtained by immunization with M52 peptide included those recognizing the N terminal region of the M52 peptide (F918-7-3); and those recognizing the C terminal region of the M52 peptide (F918-9-4). It was also demonstrated that the binding region of the F919-9-18 is present on the C terminal side of the M52 peptide site since F919-9-18 also reacts with the extracellular domain of the Fas ligand that does not include the M52 region, and F919-9-18 only reacts with those exhibiting apoptosis-inducing activity. It should 5-3 Influence of normal human serum Influence of normal human serum on the Fas ligand assay was examined for the purpose of carrying out the assay according to the procedure described in 4-2. The partially purified extracellular domain of the Fas ligand described in Example 4-1 was diluted with 0.1% BSA/PBS or normal human serum, and standard curves were prepared. As shown in FIG. 8, no difference was noted between the addition of the 0.1% BSA/PBS and the normal human serum except for the slightly lower background value with no Fas ligand addition of the normal human serum compared to the background value of the 0.1% BSA/PBS, and it was then concluded that normal human serum has no influence on the Fas ligand assay.

Figure 9:
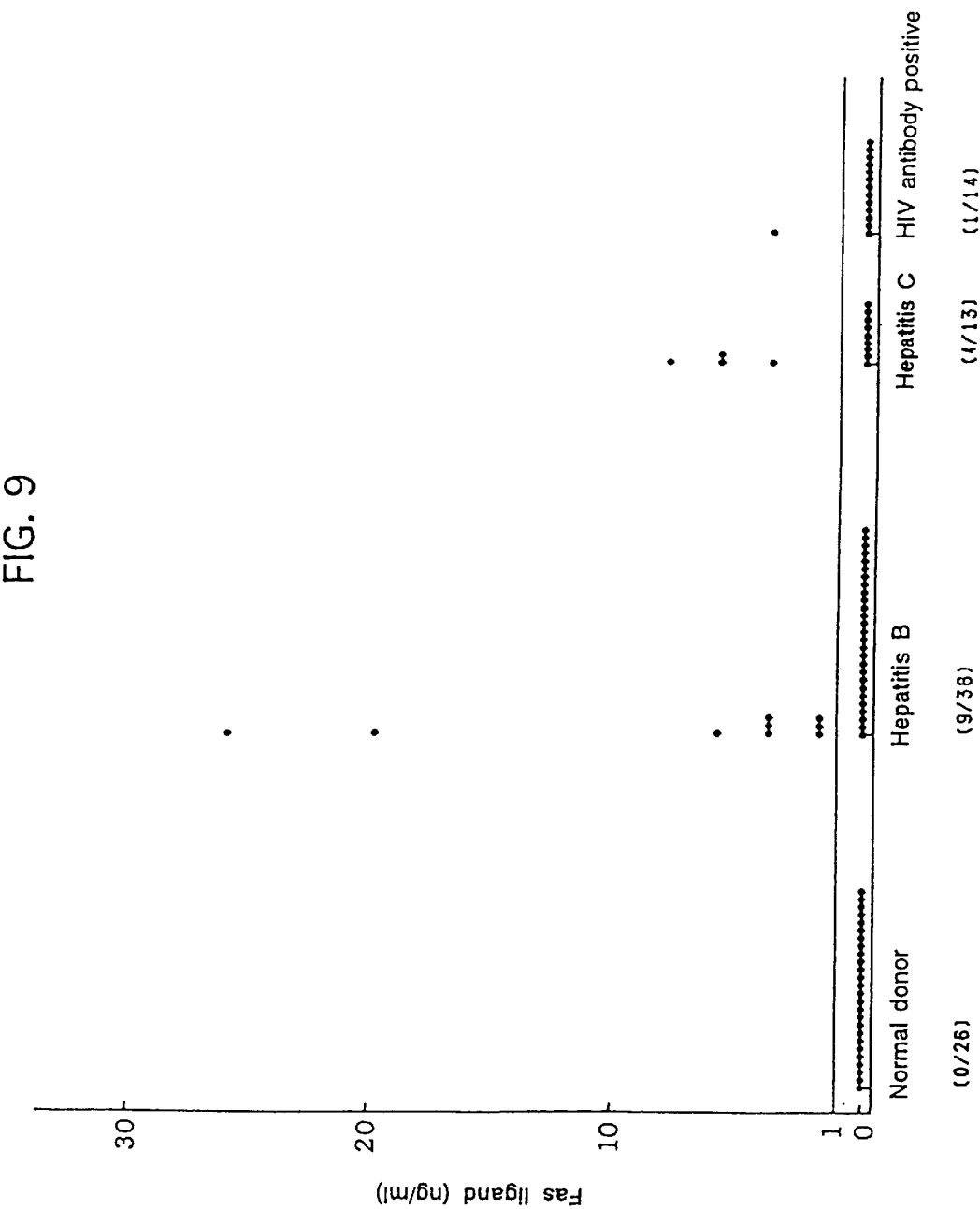
FIG. 9. A graph showing the concentrations of the Fas ligand in serums of the patients suffering from various diseases.

6. Measurement of the Fas ligand in the serum of patients suffering from various diseases Fas ligand in blood was measured by the procedure described in 4-2 using the serum of patients suffering from various diseases. The purified extracellular domain of the Fas ligand described in Example 4-1 was diluted with normal human serum to 0, 10, 50, 100, and 200 ng/ml, and the diluents were used for the standard. 26 cases of serum collected from normal donors, 36 cases of serum collected from hepatitis B patients, 13 cases of serum collected from hepatitis C patients, 14 cases of serum collected from HIV antibody positive patients, and serum collected from patients suffering from other diseases were assayed. FIG. 9 shows the measurements of different serums. Normal donors showed values below assay sensitivity (about 1 ng/ml), and high values were found in hepatitis B patients (9/36), hepatitis C patients (4/13), and HIV antibody positive patients (1/14) (In the parenthesis is shown the number of positive cases when the cut off value is set at 1 ng/ml per the number of measurements). Positive cases were also found in malaria patients (2/10), articular rheumatism patients (3/12), and anti-DNA antibody positive autoimmune disease patients (1/1) to indicate the involvement of the Fas ligand in the etiology or pathology of such diseases.

7. Cloning and sequencing of mouse F919-9-18 variable region cDNAs

Mouse F919-9-18 antibody (henceforward abbreviated F919) heavy and light chain variable region cDNAs were cloned from mRNA isolated from hybridoma cells using anchored PCR (Co et al., J. Immunol. 148: 1149 (1992)). The 5' primers used annealed to poly-dG tails added to the cDNA, and the 3' primers to the constant regions. The amplified gene fragments were then inserted into pUC18. Nucleotide sequences were determined from several independent clones for both $V_L$ and $V_H$ cDNA. For the heavy chain, a single, unique sequence was identified, typical of a mouse heavy chain variable region. For the light chain, two unique sequences, both homologous to murine light chain variable region sequences, were identified. However, one sequence was not functional because of a missing nucleotide that caused a frame shift at the V-J junction, and was identified as the n on-productive allele. The other sequence was typical of a mouse kappa chain variable region. Several clones of each sequence were sequenced and found to be respectively the same. The variable region cDNA sequences of the heavy chain and the functional light chain and the amino acid sequences derived from them are shown in FIGS. 10, 11.

8. Design of humanized F919 variable regions

To retain the binding affinity of the mouse antibody in the humanized antibody, the general procedures of Queen et al. were followed (Queen et al. *Proc. Natl. Acad. Sci. USA* 86: 10029 (1989) and European Patent EP 0451216). The choice of framework residues can be critical in retaining high binding affinity. In principle, a framework sequence from any human antibody can serve as the template for CDR grafting; however, it has been demonstrated that straight CDR replacement into such a framework can lead to significant loss of binding affinity to the antigen (Glaser et al., *J. Immunol.* 149: 2606 (1992); Tempest et al., *Biotechnology* 9: 266 (1992); Shalaby et al., *J. Exp. Med.* 17: 217 (1992)). T he more homologous a human antibody is to the original murine antibody, the less likely will the human framework introduce distortions into the mouse CDRs that could reduce affinity. Based on a sequence homology search against an antibody sequence database, the human antibody EU was chosen as providing good framework homology to the mouse F919 antibody, although other highly homologous human antibody chains would be suitable as well, especially kappa light chains from human subgroup I and heavy chains from human subgroup I (as defined by Kabat et al., Sequences of Proteins of Immunological Interest, 5th ed., U.S. Department of Health and Human Services, 1991).

The computer program ENCAD (Levitt et al., *J. Mol. Biol.* 168: 595 (1983)) was used to construct a molecular model of the F919 variable domain, which was used to locate the amino acids in the F919 framework that were close enough to the CDRs to potentially interact with them. To design the humanized F919 heavy and light chain variable regions, the CDRs from the mouse F919 antibody were grafted into the framework regions of the human EU antibody. At framework positions where the computer model suggested significant contact with the CDRs, the amino acids from the mouse antibody were substituted for the original human framework amino acids. For humanized F919, this was done at residues 27, 30, 45, 46, 68, 70, 72, and 97 of the heavy chain and at residues 7, 22, 70, 71 and 87 of the light chain. The model also showed that the two residues at position 7 and 22 of the light chain had less significant contact with the CDRs. An additional version of the humanized light chain was constructed to retain the two human framework residues (version 2), i.e., substituting T and S in positions 7 and 22 in version 1 with S and T in version 2, respectively. Results shown later indicated that there is no significant differences in binding affinities between the two versions of the light chain. The version 2 is thus a preferred choice for humanized light chain because it had retained more human residues. Furthermore, framework residues that occurred only rarely at their positions in the database of human antibodies were replaced by a human consensus amino acid at those positions. For humanized F919 this was done at residues 74, 93, 95, 98, 107, 108, 109 and 111 of the heavy chain and at residues 48 and 63 of the light chain.

The sequence of the humanized F919 antibody heavy chain and light chain (version 2) variable regions is shown in FIGS. 12, 13. However, many of the potential CDR-contact residues are amenable to substitutions of other amino acids that may still allow the antibody to retain substantial affinity to the antigen. The following table lists a number of positions in the framework where alternative amino acids may be suitable (LC=light chain, HC=heavy chain).

TABLE 4

| Position | Humanized F919 | Alternatives |
|----------|----------------|--------------|
| LC-7     | S              | T            |
| LC-22    | T              | S            |
| LC-70    | N              | E, D         |
| LC-71    | Y              | F            |
| LC-87    | F              | Y            |
| HC-27    | Y              | G            |
| HC-30    | T              | S            |
| HC-45    | F              | L            |
| HC-46    | K              | E            |
| HC-68    | F              | V            |
| HC-70    | F              | I            |
| HC-72    | L              | A            |
| HC-97    | V              | A            |

Likewise, many of the framework residues not in contact with the CDRs in the humanized F919 heavy and light chains can accommodate substitutions of amino acids from the corresponding positions of the human EU antibody, from other human antibodies, from the mouse F919 antibody, or from other mouse antibodies, without significant loss of the affinity or non-immunogenicity of the humanized antibody. The following table lists a number of additional positions in the framework where alternative amino acids may be suitable.

TABLE 5

| Position | Humanized F919 | Alternatives |
|----------|----------------|--------------|
| LC-48    | I              | M            |
| LC-63    | S              | I            |
| HC-74    | T              | E            |
| HC-93    | V              | F, T         |
| HC-95    | Y              | F            |
| HC-98    | R              | G            |
| HC-107   | W              | E            |
| HC-108   | G              | Y            |
| HC-109   | Q              | N            |
| HC-111   | T              | G            |

Selection of combinations of alternative amino acids may be used to produce versions of humanized F919 that have varying combinations of affinity, specificity, non-immunogenicity, ease of manufacture, and other desirable properties. Thus, the examples in the above tables are offered by way of illustration, not of limitation.

9. Construction of humanized F919

Once the humanized variable region amino acid sequences had been designed as described above, genes were constructed to encode them, including signal peptides, splice donor signals and appropriate restriction sites (FIGS. 12 and 13). The heavy chain variable region gene was constructed and amplified using eight overlapping synthetic oligonucleotides ranging in length from 61 to 79 bases. The oligos were annealed pairwise and extended with the Klenow fragment of DNA polymerase I, yielding four double-stranded fragments. The resulting fragments were denatured, annealed, and extended with Klenow, yielding two fragments. These fragments were denatured, annealed pairwise, and extended once again, yielding a full-length gene. The resulting product was amplified by polymerase chain reaction (PCR) using Taq polymerase, gel-purified, digested with XbaI, gel-purified again, and subcloned into the XbaI site of the pVg1 (see Co et al., J. Immunol. 148: 1149 (1992)) or pVg4 expression vector. The pVg4 vector was constructed by replacing the XbaI-BamHI fragment of pVg1 containing the γ1 constant region gene with an approximately 2000 bp fragment of the human γ4 constant region gene (Ellison and Hood, Proc. Natl. Acad. Sci. USA 79: 1984 (1982)) that extended from the HindIII site preceding the $C_H1$ exon of the γ4 gene to 270 bp after the NsiI site following the $C_H4$ exon of the gene. The resulting plasmids were verified by nucleotide sequencing and restriction mapping.

The light chain variable region gene was constructed in an alternate manner. The designed light chain variable region sequence was found to be highly homologous to HuC4G1, a humanized antibody specific for gpIIb/IIIa which was previously constructed (M. S. Co et. al., J. Immunol. 152: 2968 (1994)). The HuC4G1 light chain and the HuF919 light chain (version 1) differ by only four amino acid residues at positions 30, 53, 70 and 92 in the entire variable region. We therefore constructed the HuF919 light chain variable region gene by incorporating the desired amino acid residues at those four positions into the previously constructed HuC4G1 light chain gene in the pVk plasmid by site-directed mutagenesis using synthetic oligonucleotides and PCR. The second version of the light chain had two additional differences at positions 7 and 22 and was constructed in a similar fashion. Th e resulting plasmids therefore contain each humanized F919 variable region gene in the pVk vector containing the human $C_k$ gene (see Co et al., ibid.). The final plasmids were also verified by nucleotide sequencing and restriction mapping. All manipulations were performed by standard methods well-known to those skilled in the art.

Four humanized F919 anti bodies w ere therefore constructed by the different combinations of the heavy chains and the light chains as shown below:

TABLE 6

| Antibody Designation | Heavy chain | Light chain |
| --- | --- | --- |
| HuF919G1.v1 | gamma 1 chain | kappa chain version 1 |
| HuF919G1.v2 | gamma 1 chain | kappa chain version 2 |
| HuF919G4.v1 | gamma 4 chain | kappa chain version 1 |
| HuF919G4.v2 | gamma 4 chain | kappa chain version 2 |

To construct a cell line producing each of the above antibodies, the respective heavy chain and light chain plasmids were transfected into a mouse myeloma cell line Sp2/0-Ag14 (ATCC CRL 1581). Before transfection, the heavy and light chain-containing plasmids were linearized using BamHI and FspI, respectively. Approximately 20 μg of each plasmid was transfected into 1×10⁷ cells in PBS. Transfection was by electroporation using a Gene Pulser apparatus (BioRad) at 360 V and 25 μFD capacitance according to the manufacturer's instructions. The cells from each transfection were plated in four 96-well tissue culture plates, and after two days, selection medium (DMEM, 10% FCS, 1×HT supplement (Sigma), 0.25 mg/ml xanthine, 1 μg/ml mycophenolic acid) was applied.

After approximately two weeks, the clones that appeared were screened for antibody production by ELISA. Antibody from a high-producing clone from each transfection was prepared by growing the cells to confluency in regular medium (DMEM with 10% FCS), then replacing the medium with a serum-free medium (Hybridoma SMF; Gibco) and culturing until maximum antibody titers were achieved in the culture. The culture supernatant was run through a protein A-Sepharose column (Pharmacia); antibody was eluted with 0.1 M glycine, 0.1 M NaCl, pH 2.7 and subsequently exchanged into phosphate-buffered saline (PBS). The purity of the antibody was verified by analyzing it on an acrylamide gel, and its concentration was determined by an $OD_{280}$ reading, assuming 1.0 mg of antibody protein has an $OD_{280}$ reading of 1.3.

10. Properties of humanized F919

To show that the murine and the humanized F919 antibodies bind to the Fas ligand antigen, 25 ng of each antibody (murine F919, HuF919G1.v1, HuF919G1.v2, HuF919G4.v1 and HuF919G4.v2) were each incubated on ice for 30 minutes with 1A12 cells, a mouse lymphoma cell line WR19L transfected with and expressing the Fas ligand. The cells were washed with cold PBS, incubated for an additional 30 minutes with FITC-labelled goat-anti-human or anti-mouse antibodies (Tago Immunologicals) and analyzed by flow cytometry (FACS). The FACS histograms demonstrated that the murine and the four humanized F919 antibodies bound specifically to the 1A12 cells but did not bind to the non-transfected cell line WR19L.

Figure 14:
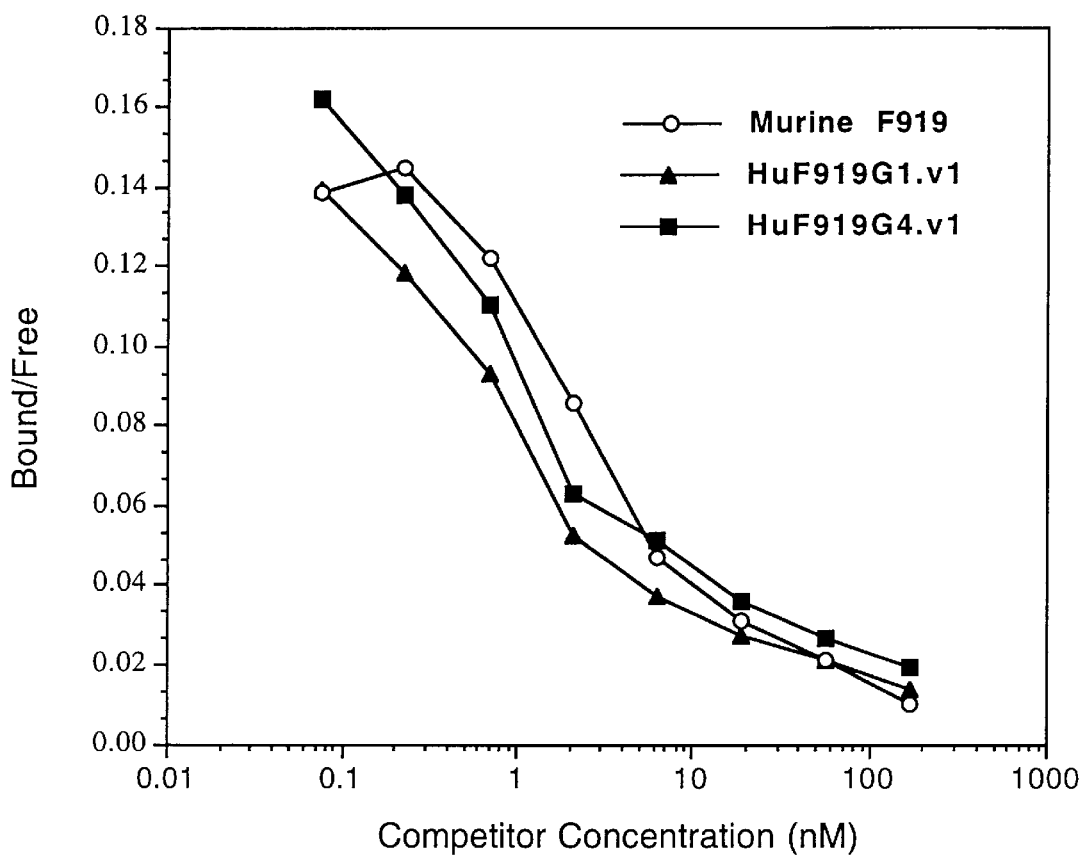
FIG. 14. Competitive binding of murine and humanized F919 antibodies, versions 1. Increasing concentrations of cold competitor antibodies were incubated with the 1A12 transfectant cells expressing Fas ligand in the presence of radiolabeled tracer mouse F919 antibody, and the ratio of bound/free radioactivity determined. The results shown are mean values of duplicate samples.
Figure 15:
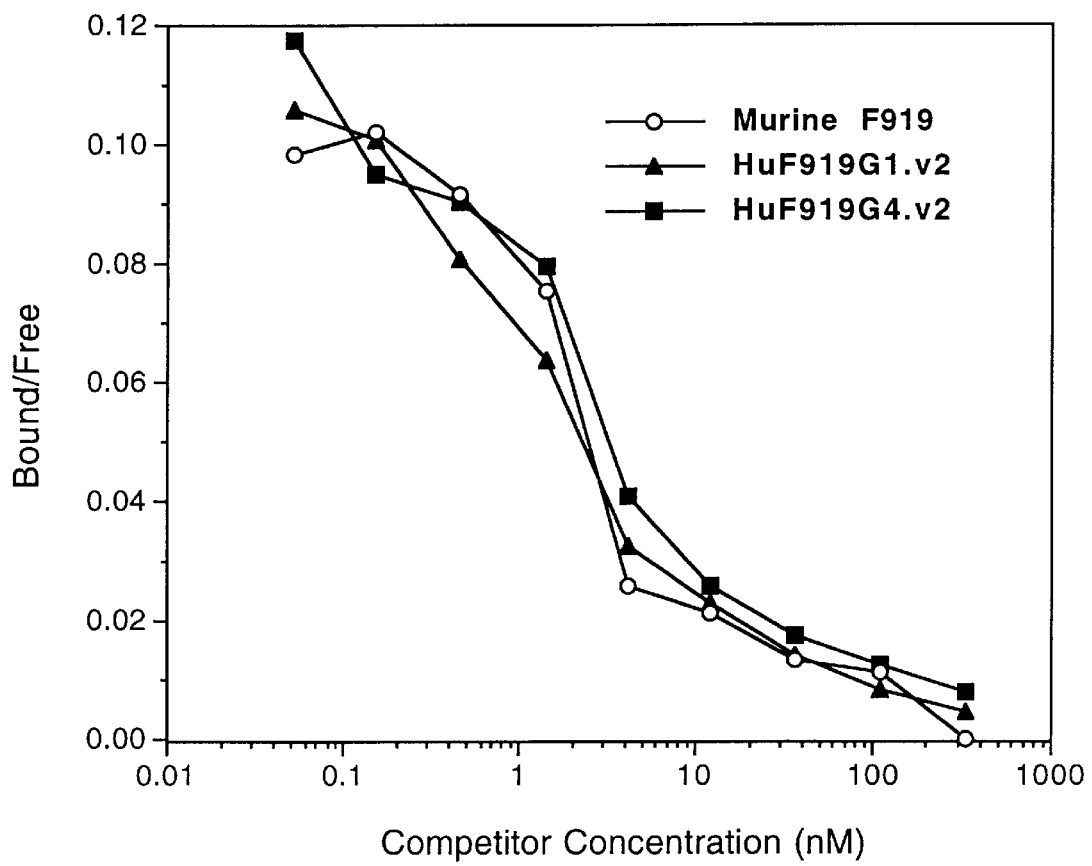
FIG. 15. Competitive binding of murine and humanized F919 antibodies, versions 2. Increasing concentrations of cold competitor antibodies were incubated with the 1A12 transfectant cells expressing Fas ligand in the presence of radiolabeled tracer mouse F919 antibody, and the ratio of bound/free radioactivity determined. The results shown are mean values of duplicate samples.

To assess the ability of the humanized F919 antibodies to compete with the mouse F919 antibody for receptor binding, increasing concentrations (0.01–50 ug/ml) of the murine F919 antibody and each version of the humanized F919 antibody were respectively incubated at 4° C. for 90 min with 5×10⁵ 1A12 cells and a fixed amount (5 ng) of tracer $^{125}$I-labelled murine antibody. The murine and humanized F919 antibodies competed with essentially equal efficiencies (FIGS. 14–15). The binding affinities calculated from the data were very similar, as shown in the following table. Thus the humanization procedure did not significantly alter the binding affinity of the original antibody.

TABLE 7

| Antibody | Affinity ($K_a$) |
| --- | --- |
| Murine | $3 - 4 \times 10^8$ M$^{-1}$ |
| HuF919G1.v1 | $6 \times 10^8$ M$^{-1}$ |
| HuF919G1.v2 | $4 \times 10^8$ M$^{-1}$ |
| HuF919G4.v1 | $5 \times 10^8$ M$^{-1}$ |
| HuF919G4.v2 | $3 \times 10^8$ M$^{-1}$ |

11. Evaluation of humanized F919 antibodies

The apoptosis-suppressing activity of humanized F919 antibodies was measured by using the inhibitory activity for cytotoxicity of 1A12 cells against WC8 cells for the index. 1A12 cells are transformants of mouse WR19L cells transformed to express human Fas ligand (Tanaka M. et al., Nature Medicine 2:317–322,1996), and WC8 cells are the transformants of WR19L cells transformed to express human Fas antigen. The WR19L cells hardly express mouse Fas antigen and are sensitive for cytotoxic action of TNF. The cytotoxicity was examined according to the method described by Rouvier E. et al. (J. Exp. Med., 177: 195–200, 1993). First, 1A12 cells were washed with RPMI 1640 medium containing 10% heat-inactivated fetal bovine serum (FBS), and used for effector cells. On the other hand, WC8 cells were incubated at 37° C. for 2 hours with 20μ Ci of [$^{51}$Cr] sodium chromate (NEN)=in 100 μl of 10% FBS-containing RPMI 1640 medium, subsequently washed with 10% FBS-containing RPMI 1640 medium and used for target cells. 1A12 cells and WC8 cells were incubated with increasing concentrations (0.01–1 μg/ml) of mouse or humanized F919 antibody in total volume of 100 μl at 37° C. for 4 hours. Using the formula shown below, the specific lysis was calculated from the radioactivity of the culture supernatant in each well. The spontaneous $^{51}$Cr release was measured by incubating target cells in medium alone, and the maximum $^{51}$Cr release was measured by solubilizing target cells with 0.1% Triton X-100.

$$\text{Specific lysis (\%)} = \frac{\text{Actual }^{51}\text{Cr release} - \text{spontaneous }^{51}\text{Cr release}}{\text{Maximum }^{51}\text{Cr release} - \text{spontaneous }^{51}\text{Cr release}} \times 100$$

Figure 16:
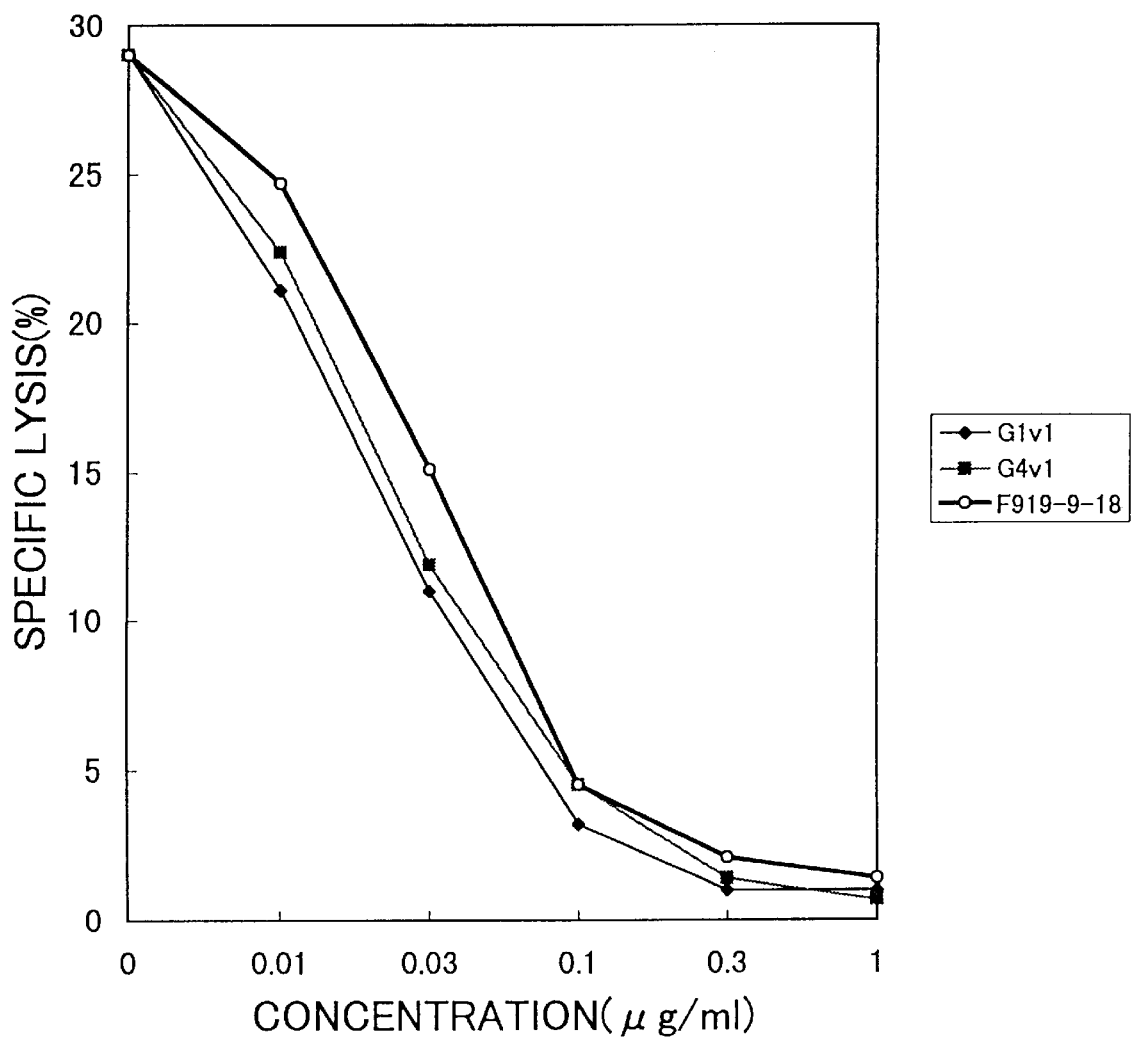
FIG. 16. Apoptosis-suppressing activity of mouse F919 and humanized F919 antibodies (Version 1). The results shown were mean values of triplicate samples.
Figure 17:
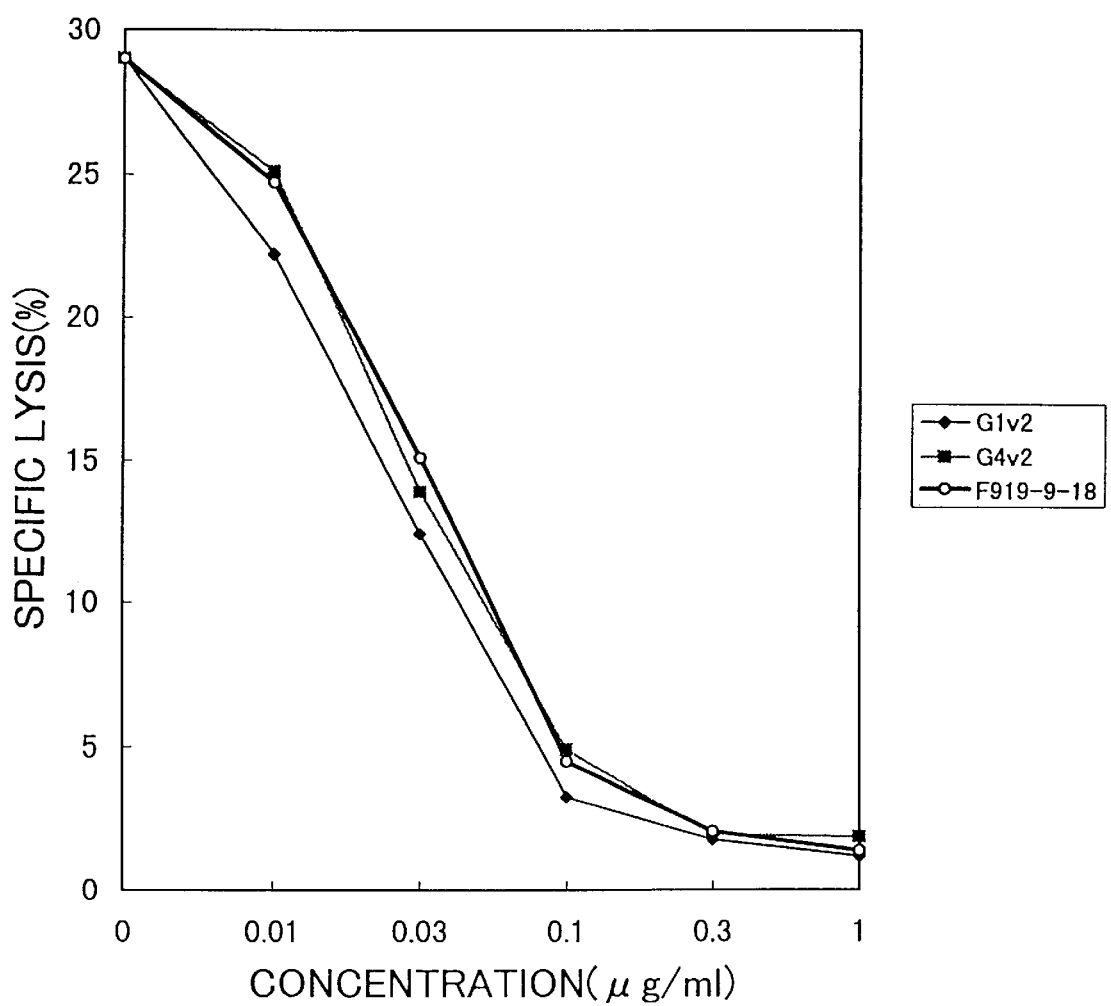
FIG. 17. Apoptosis-suppressing activity of mouse F919 and humanized F919 antibodies (Version 2). The results shown were mean values of triplicate samples.

As demonstrated in FIGS. 16 and 17, each of the humanized F919 antibodies showed a suppressing activity almost the same as or a little stronger than the mouse F919 antibody.

MERITS OF THE INVENTION

The method for assaying the Fas ligand in human body fluid utilizing an anti-Fas ligand antibody, and the antibody used in such assay method according to the present invention can be used for detecting an increase/decrease or abnormality in the amount of the Fas ligand associated with various diseases wherein involvement of the Fas ligand has been indicated, and therefore, the assay method and the antibody of the present invention can be used for prediction, detection and diagnosis of particular diseases and their pathological conditions, and for selection of an adequate therapy. The assay method and the antibody of the present invention is also useful for the monitoring, and for the determination of the therapeutical effects and prognosis of the patients who have been treated with a Fas ligand, a Fas ligand-related substance, or a reagent that affects the Fas ligand expression.

An antibody that regulates the action of the Fas ligand can be used for the regulation of the apoptosis induced by an endogenous or exogenous Fas ligand that takes place in the body, and hence, for the treatment and diagnosis of the disease. The anti-Fas ligand antibody that promotes the Fas ligand-induced apoptosis can be used for removing the cells that are unnecessary for the body. For example, as described in the foregoing, AIDS virus-infected cells express Fas antigen, and therefore, AIDS in its early phase may be treated with such an anti-Fas ligand antibody that artificially promotes the Fas ligand-induced apoptosis and the removal of the infected cells at an earlier stage. In other autoimmune diseases, autoantigen reactive T cells may be removed by artificially promoting the Fas ligand-induced apoptosis mediated by the Fas antigen. The anti-Fas ligand antibody that promotes the Fas ligand-induced apoptosis should also be useful in the therapy of cancers in view of Morimoto, H. et al. (Cancer Res., vol. 53, 2591–2596, 1993) reporting the synergistic carcinostatic effects brought about by the induction of the Fas antigen-mediated apoptosis of the cancer cells with the administration of adriamycin and cisplatin.

Humanized antibodies of the present invention have at least three potential advantages over mouse and in some cases chimeric antibodies for use in human therapy:

1) because the effector portion is human, it may interact better with the other parts of the human immune system (e.g., destroy the target cells more efficiently by complement-dependent cytotoxicity (CDC) or antibody-dependent cellular cytotoxicity (ADCC).

2) The human immune system should not recognize the framework or C region of the humanized antibody as foreign, and therefore the antibody response against such an injected antibody should be less than against a totally foreign mouse antibody or a partially foreign chimeric antibody.

3) Injected humanized antibodies will presumably have a half-life more like that of naturally occurring human antibodies, allowing smaller and less frequent doses to be given.

On the other hand, reduced immunological competence in late stages of AIDS virus infections and liver dysfunction in fulminant hepatitis are considered to be the results of the dysfunction of the immunocytes and the dysfunction of the liver tissue caused by the apoptosis of the hepatocytes. Under such pathological conditions, it would be necessary to suppress the action of the Fas ligand to thereby prevent the apoptosis of the cells. Use of the anti-Fas ligand antibody that suppresses the Fas ligand-induced apoptosis should be useful for the treatment of such pathological conditions. The anti-Fas ligand neutralizing antibody of the present invention exhibits a strong apoptosis-suppressing effects at a low concentration, and therefore, the neutralizing antibody of the present invention is expected to suppress the side effects at a low dosage while attaining the desired therapeutical effects in the body. High effectivity, safety, and cost performance would then be achieved.

Use of the Fas ligand itself for the treatment and the research should require the production of the Fas ligand protein of high purity in a large quantity. The anti-Fas ligand antibody of the present invention is useful for the purification of such Fas ligand. The anti-Fas ligand antibody of the present invention is particularly useful in the specific, high-efficiency purification of the active Fas ligand without impairing its activity, and it is such an active Fas ligand that should serve an important therapeutic reagent.

What is claimed is:

1. An anti-Fas ligand antibody which suppresses Fas ligand-induced apotosis of Fas antigen-expressing cells to an apoptosis suppression rate of 50% or higher at a final concentration of 1 µg/ml of anti-Fas ligand antibody in an in vitro assay at a final concentration of 0.09 µg/ml of human Fas ligand extracellular domain.

2. An anti-Fas ligand antibody which reacts with a Fas ligand with apoptosis-inducing activity and which does not react with a Fas ligand without apoptosis-inducing activity.

3. The anti-Fas ligand antibody according to claim 1 which binds to human Fas ligand with an affinity constant of at least $10^7 M^{-1}$.

4. A humanized anti-Fas ligand antibody which suppresses Fas ligand-induced apoptosis of Fas antigen expressing cells in vitro to a suppression rate of 50% or higher at a concentration of 0.09 µg/ml of human Fas ligand extracellular domain and which comprises complementarity determining regions (CDRs) comprising SEQ ID NO:13, SEQ ID NO:15, SEQ ID NO:19, SEQ ID NO:21 and SEQ ID NO:23 as shown in FIG. 10 or FIG. 11.

5. An anti-Fas ligand antibody which specifically reacts with one peptide selected from the group consisting of SEQ ID NO:1, SEQ ID NO:2, SEQ ID NO:3, SEQ ID NO:4, SEQ ID NO:5, SEQ ID NO:6, SEQ ID NO:7, and SEQ ID NO:8.

6. The anti-Fas ligand antibody according to claim 5 which specifically reacts with the peptide of SEQ ID No.1, and which does not react a peptide selected from the group consisting of SEQ ID NO: 2, SEQ ID NO:3, SEQ ID NO:4, SEQ ID NO:5, SEQ ID NO:7 and SEQ ID NO:8.

7. The anti-Fas ligand antibody according to claim 5 which specifically reacts with the peptide of SEQ ID No. 6, and which does not react with the peptides of SEQ ID Nos. 1 to 5 and SEQ ID Nos. 7 to 8.

8. An anti-Fas ligand antibody which is a humanized immunoglobulin (Ig) comprising a human acceptor framework region (FR) and a CDR from a non-human donor Ig which specifically binds to human Fas ligand.

9. The anti-Fas ligand antibody according to claim 8 which suppresses Fas ligand-induced apoptosis of Fas antigen-expressing cells.

10. An anti-Fas ligand antibody according to claim 8 wherein the amino acid sequence of the humanized immunoglobulin heavy chain variable region framework is more than 65% identical but less than 95% identical to the amino acid sequence of the non-human donor immunoglobulin heavy chain variable region framework.

11. The anti-FAS ligand antibody according to claim 8 wherein said antibody contains a human amino acid sequence in the acceptor immunoglobulin heavy chain variable region that is among the 5 sequences in a representative collection of sequences of human immunoglobulin heavy chain variable regions most homologous to a corresponding amino acid sequence of the non-human donor immunoglobulin heavy chain variable region.

12. An anti-Fas ligand antibody according to claim 8 wherein said humanized immunoglobulin comprises an amino acid from the donor immunoglobulin framework replacing the corresponding amino acid in the acceptor immunoglobulin heavy or light chain frameworks, said amino acid is not in positions 26–30 of the heavy chain in the acceptor immunoglobulin, and each of said amino acids:
 (i) is immediately adjacent sequenced amino acid to a CDR in the donor immunoglobulin amino acid sequence, or
 (ii) contains an atom of the amino acid within a distance of about 5 angstroms of a CDR in a tertiary structure immunoglobulin model.

13. A method for assaying a Fas ligand wherein an anti-Fas ligand antibody is used for the assay of the Fas ligand in human body fluid.

14. The method for assaying a Fas ligand according to claim 13 wherein increase or decrease in quantity of the Fas ligand in human body fluid is measured to thereby predict, detect, or diagnose a dysfunction in Fas antigen/Fas ligand system, a disease involving such dysfunction, or pathology of such disease.

15. The assay method according to claim 14 wherein said disease is selected from the group consisting of hepatitis B, hepatitis C, and HIV infection.

16. A method for assaying Fas ligand which comprises: contacting said anti-Fas ligand antibody according to any one of claims 2 to 8 with a human body fluid and detecting the presence of the said Fas ligand.

17. A method for assaying Fas ligand which comprises: contacting two or more anti-Fas ligand antibodies of the same type or different types according to any one of claims 1 to 4 with a human body fluid and detecting the presence of the Fas ligand.

18. A method for assaying Fas ligand which comprises: contacting two or more anti-Fas ligand antibodies of the same type or different types according to any one of claims 5 to 7 with human body fluid and detecting the presence of the Fas ligand.

19. A method for assaying Fas ligand which comprises: contacting one or more anti-Fas ligand antibodies according to any one of claims 1 to 4 and one or more anti-Fas ligand antibodies which specifically react with a peptide selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8 with human body fluid and detecting the presence of the Fas ligand.

20. The assay method according to claim 16 wherein said assay is carried out by sandwich method.

21. A hybridoma or a cell line which produces the antibody according to any one of claims 1 to 12.

22. A composition comprising an antibody according to any one of claims 1 to 7 and a carrier for the antibody.

23. A method for treating systemic or topical pathological conditions, caused by the abnormality of Fas/Fas ligand system in a disease wherein an apoptosis is induced by Fas ligand in Fas antigen-expressing cells, which comprises administering to a patient a therapeutically-effective dose of an anti-Fas ligand antibody which suppresses Fas ligand-induced apoptpsis of Fas antigen-expressing cells.

* * * * *

SEQUENCE LISTING (1) GENERAL INFORMATION:

(iii) NUMBER OF SEQUENCES: 41

(2) INFORMATION FOR SEQ ID NO:1:

-continued

```
    (i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ser Leu Glu Lys Gln Ile Gly His Pro Ser Pro Pro Glu Lys Lys
1               5                  10                  15

Glu Leu Arg Lys
            20

(2) INFORMATION FOR SEQ ID NO:2:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Leu Thr Gly Lys Ser Asn Ser Arg Ser Met Pro Leu Glu Trp
1               5                  10

(2) INFORMATION FOR SEQ ID NO:3:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Trp Glu Asp Thr Tyr Gly Ile Val Leu Leu Ser Gly Val
1               5                  10

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Leu Val Ile Asn Glu Thr Gly Leu Tyr Phe Val
1               5                  10

(2) INFORMATION FOR SEQ ID NO:5:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Val Tyr Ser Lys Val Tyr Phe Arg Gly Gln Ser Cys Asn Asn Leu Pro
1               5                  10                  15
```

-continued

```
    Leu Ser His (2) INFORMATION FOR SEQ ID NO:6:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Lys Val Tyr Met Arg Asn Ser Lys Tyr Pro Gln Asp Leu Val Met Met
    1               5                  10                  15

Glu Gly (2) INFORMATION FOR SEQ ID NO:7:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Lys Met Met Ser Tyr Cys Thr Thr Gly Gln Met Trp Ala Arg Ser Ser
    1               5                  10                  15

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Leu Val Asn Phe Glu Glu Ser Gln Thr Phe Phe
    1               5                  10

(2) INFORMATION FOR SEQ ID NO:9:

(i) SEQUENCE CHARACTERISTICS:
        (A) LENGTH: 179 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

Gln Leu Phe His Leu Gln Lys Glu Leu Ala Glu Leu Arg Glu Ser Thr
    1               5                  10                  15

Ser Gln Met His Thr Ala Ser Ser Leu Glu Lys Gln Ile Gly His Pro
                    20                  25                  30

Ser Pro Pro Pro Glu Lys Lys Glu Leu Arg Lys Val Ala His Leu Thr
                35                  40                  45

Gly Lys Ser Asn Ser Arg Ser Met Pro Leu Glu Trp Glu Asp Thr Tyr
            50                  55                  60

Gly Ile Val Leu Leu Ser Gly Val Lys Tyr Lys Lys Gly Gly Leu Val
    65                  70                  75                  80
```

```
    Ile Asn Glu Thr Gly Leu Tyr Phe Val Tyr Ser Lys Val Tyr Phe Arg
                    85                  90                  95

Gly Gln Ser Cys Asn Asn Leu Pro Leu Ser His Lys Val Tyr Met Arg
                100                 105                 110

Asn Ser Lys Tyr Pro Gln Asp Leu Val Met Met Glu Gly Lys Met Met
                115                 120                 125

Ser Tyr Cys Thr Thr Gly Gln Met Trp Ala Arg Ser Ser Tyr Leu Gly
                130                 135                 140

Ala Val Phe Asn Leu Thr Ser Ala Asp His Leu Tyr Val Asn Val Ser
    145                 150                 155                 160

Glu Leu Ser Leu Val Asn Phe Glu Glu Ser Gln Thr Phe Phe Gly Leu
                    165                 170                 175

Tyr Lys Leu (2) INFORMATION FOR SEQ ID NO:10:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Asp Ile Gln Met Thr Gln Thr Thr Ser Ser Leu Ser Ala Ser Leu Gly
    1               5                   10                  15

Asp Arg Val Thr Ile Ser Cys
                20

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Arg Ala Ser Gln Asp Ile Ser Asn Tyr Leu Asn
    1               5                   10

(2) INFORMATION FOR SEQ ID NO:12:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

Trp Tyr Gln Gln Lys Pro Asp Gly Thr Val Lys Leu Leu Ile Tyr
    1               5                   10                  15

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear
```

```
    (ii) MOLECULE TYPE: peptide (xi) SEQUENCE DESCRIPTION: SEQ ID NO:13:

Tyr Thr Ser Arg Leu His Ser
    1               5

(2) INFORMATION FOR SEQ ID NO:14:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gly Val Pro Ser Arg Phe Ser Gly Ser Gly Ser Gly Thr Asn Tyr Ser
    1               5                   10                  15

Leu Thr Ile Ser Asn Leu Glu Gln Gly Asp Ile Ala Thr Tyr Phe Cys
                    20                  25                  30

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Gln Gln Gly Ser Thr Leu Pro Trp Thr
    1               5

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Phe Gly Gly Gly Thr Lys Leu Glu Ile Lys
    1               5                   10

(2) INFORMATION FOR SEQ ID NO:17:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Met Met Ser Ser Ala Gln Phe Leu Gly Leu Leu Leu Leu Cys Phe Gln
    1               5                   10                  15

Gly Thr Arg Cys Asp Ile Gln Met Thr Gln Thr Thr Ser Ser Leu Ser
                    20                  25                  30

Ala Ser Leu Gly Asp Arg Val Thr Ile Ser Cys Arg Ala Ser Gln Asp
                    35                  40                  45
```

```
Ile Ser Asn Tyr Leu Asn Trp Tyr Gln Gln Lys Pro Asp Gly Thr Val
    50                  55                  60
Lys Leu Leu Ile Tyr Tyr Thr Ser Arg Leu His Ser Gly Val Pro Ser
65                  70                  75                  80
Arg Phe Ser Gly Ser Gly Ser Gly Thr Asn Tyr Ser Leu Thr Ile Ser
                85                  90                  95
Asn Leu Glu Gln Gly Asp Ile Ala Thr Tyr Phe Cys Gln Gln Gly Ser
            100                 105                 110
Thr Leu Pro Trp Thr Phe Gly Gly Gly Thr Lys Leu Glu Ile Lys
            115                 120                 125
```

(2) INFORMATION FOR SEQ ID NO:18:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr
            20                  25                  30
```

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Glu Tyr Pro Met His
1               5
```

(2) INFORMATION FOR SEQ ID NO:20:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Trp Val Lys Gln Ala Pro Gly Lys Gly Phe Lys Trp Met Gly
1               5                   10
```

(2) INFORMATION FOR SEQ ID NO:21:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Met Ile Tyr Thr Asp Thr Gly Glu Pro Ser Tyr Ala Glu Glu Phe Lys
```

```
              1               5              10              15

Gly (2) INFORMATION FOR SEQ ID NO:22:

(i) SEQUENCE CHARACTERISTICS:
         (A) LENGTH: 32 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:22:

Arg Phe Ala Phe Ser Leu Glu Thr Ser Ala Ser Thr Ala Tyr Leu Gln
    1               5                  10                  15

Ile Asn Phe Leu Lys Asn Glu Asp Thr Ala Thr Tyr Phe Cys Val Arg
                    20                  25                  30

(2) INFORMATION FOR SEQ ID NO:23:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:23:

Phe Tyr Trp Asp Tyr Phe Asp Tyr
    1               5

(2) INFORMATION FOR SEQ ID NO:24:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:24:

Trp Gly Gln Gly Thr Thr Leu Thr Val Ser Ser
    1               5                  10

(2) INFORMATION FOR SEQ ID NO:25:

(i) SEQUENCE CHARACTERISTICS:
         (A) LENGTH: 136 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:25:

Met Asp Trp Val Trp Thr Leu Leu Phe Leu Ile Ala Ala Ala Gln Ser
    1               5                  10                  15

Ala Gln Ala Gln Ile Gln Leu Val Gln Ser Gly Pro Glu Leu Lys Lys
                    20                  25                  30

Pro Gly Glu Thr Val Lys Ile Ser Cys Lys Ala Ser Gly Tyr Thr Phe
                35                  40                  45

Thr Glu Tyr Pro Met His Trp Val Lys Gln Ala Pro Gly Lys Gly Phe
            50                  55                  60
```

```
Lys Trp Met Gly Met Ile Tyr Thr Asp Thr Gly Glu Pro Ser Tyr Ala
 65                  70                  75                  80

Glu Glu Phe Lys Gly Arg Phe Ala Phe Ser Leu Glu Thr Ser Ala Ser
                 85                  90                  95

Thr Ala Tyr Leu Gln Ile Asn Phe Leu Lys Asn Glu Asp Thr Ala Thr
            100                 105                 110

Tyr Phe Cys Val Arg Phe Lys Trp Asp Tyr Phe Asp Tyr Trp Gly Gln
            115                 120                 125

Gly Thr Thr Leu Thr Val Ser Ser
            130             135
```

(2) INFORMATION FOR SEQ ID NO:26:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Asp Ile Gln Met Thr Gln Ser Pro Ser Thr Leu Ser Ala Ser Val Gly
 1               5                  10                  15

Asp Arg Val Thr Ile Thr Cys
            20
```

(2) INFORMATION FOR SEQ ID NO:27:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Arg Ala Ser Gln Asp Ile Ser Asn Tyr Leu Asn
 1               5                  10
```

(2) INFORMATION FOR SEQ ID NO:28:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
Trp Tyr Gln Gln Lys Pro Gly Lys Ala Pro Lys Leu Leu Ile Tyr
 1               5                  10                  15
```

(2) INFORMATION FOR SEQ ID NO:29:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

```
Tyr Thr Ser Arg Leu His Ser
```

```
          1               5

(2) INFORMATION FOR SEQ ID NO:30:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Gly Val Pro Ser Arg Phe Ser Gly Ser Gly Ser Thr Asn Tyr Thr
  1               5                  10                  15

Leu Thr Ile Ser Ser Leu Gln Pro Asp Asp Phe Ala Thr Tyr Phe Cys
                  20                  25                  30

(2) INFORMATION FOR SEQ ID NO:31:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

Gln Gln Gly Ser Thr Leu Pro Trp Thr
  1               5

(2) INFORMATION FOR SEQ ID NO:32:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Phe Gly Gln Gly Thr Lys Val Glu Val Lys
  1               5                  10

(2) INFORMATION FOR SEQ ID NO:33:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Met Glu Thr Asp Thr Leu Leu Leu Trp Val Leu Leu Leu Trp Val Pro
  1               5                  10                  15

Gly Ser Thr Gly Asp Ile Gln Met Thr Gln Ser Pro Ser Thr Leu Ser
                  20                  25                  30

Ala Ser Val Gly Asp Arg Val Thr Ile Thr Cys Arg Ala Ser Gln Asp
                  35                  40                  45

Ile Ser Asn Tyr Leu Asn Trp Tyr Gln Gln Lys Pro Gly Lys Ala Pro
                  50                  55                  60

Lys Leu Leu Ile Tyr Tyr Thr Ser Arg Leu His Ser Gly Val Pro Ser
  65                  70                  75                  80
```

```
        Arg Phe Ser Gly Ser Gly Ser Gly Thr Asn Tyr Thr Leu Thr Ile Ser
                        85                  90                  95

Ser Leu Gln Pro Asp Asp Phe Ala Thr Tyr Phe Cys Gln Gln Gly Ser
                        100                 105                 110

Thr Leu Pro Trp Thr Phe Gly Gln Gly Thr Lys Val Glu Val Lys
                        115                 120                 125
```

(2) INFORMATION FOR SEQ ID NO:34:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
        Gln Val Gln Leu Val Gln Ser Gly Ala Glu Val Lys Lys Pro Gly Ser
        1               5                   10                  15

Ser Val Lys Val Ser Cys Lys Ala Ser Gly Tyr Thr Phe Thr
                        20                  25                  30
```

(2) INFORMATION FOR SEQ ID NO:35:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
        Glu Tyr Pro Met His
        1               5
```

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

```
        Trp Val Arg Gln Ala Pro Gly Gln Gly Phe Lys Trp Met Gly
        1               5                   10
```

(2) INFORMATION FOR SEQ ID NO:37:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

```
        Met Ile Tyr Thr Asp Thr Gly Gln Pro Ser Tyr Ala Glu Glu Phe Lys
        1               5                   10                  15

Gly
```

(2) INFORMATION FOR SEQ ID NO:38:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

```
Arg Phe Thr Phe Thr Leu Asp Thr Ser Thr Asn Thr Ala Tyr Met Glu
 1               5                  10                  15

Leu Ser Ser Leu Arg Ser Glu Asp Thr Ala Val Tyr Tyr Cys Val Arg
                20                  25                  30
```

(2) INFORMATION FOR SEQ ID NO:39:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:39:

```
Phe Tyr Trp Asp Tyr Phe Asp Tyr
 1               5
```

(2) INFORMATION FOR SEQ ID NO:40:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:40:

```
Trp Gly Gln Gly Thr Leu Val Thr Val Ser Ser
 1               5                  10
```

(2) INFORMATION FOR SEQ ID NO:41:

(i) SEQUENCE CHARACTERISTICS:
        (A) LENGTH: 136 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:41:

```
Met Asp Trp Val Trp Thr Leu Leu Phe Leu Ile Ala Ala Ala Gln Ser
 1               5                  10                  15

Ala Gln Ala Gln Val Gln Leu Val Gln Ser Gly Ala Glu Val Lys Lys
                20                  25                  30

Pro Gly Ser Ser Val Lys Val Ser Cys Lys Ala Ser Gly Tyr Thr Phe
                35                  40                  45

Thr Glu Tyr Pro Met His Trp Val Arg Gln Ala Pro Gly Gln Gly Phe
         50                  55                  60

Lys Trp Met Gly Met Ile Tyr Thr Asp Thr Gly Glu Pro Ser Tyr Ala
 65              70                  75                  80

Glu Glu Phe Lys Gly Arg Phe Thr Phe Thr Leu Asp Thr Ser Thr Asn
                85                  90                  95
```

```
Thr Ala Tyr Met Glu Leu Ser Ser Leu Arg Ser Glu Asp Thr Ala Val
            100                 105                 110

Tyr Tyr Cys Val Arg Phe Tyr Trp Asp Tyr Phe Asp Tyr Trp Gly Gln
        115                 120                 125

Gly Thr Leu Val Thr Val Ser Ser
130                 135
```